(12) United States Patent
Okazaki

(10) Patent No.: US 10,048,283 B2
(45) Date of Patent: Aug. 14, 2018

(54) METHOD FOR ANALYZING LIPOPROTEINS

(71) Applicant: Mitsuyo Okazaki, Ichikawa (JP)

(72) Inventor: Mitsuyo Okazaki, Ichikawa (JP)

( * ) Notice: Subject to any disclaimer, the term of this patent is extended or adjusted under 35 U.S.C. 154(b) by 0 days.

(21) Appl. No.: 15/301,916

(22) PCT Filed: Apr. 2, 2015

(86) PCT No.: PCT/JP2015/060467
§ 371 (c)(1),
(2) Date: Oct. 4, 2016

(87) PCT Pub. No.: WO2015/152371
PCT Pub. Date: Oct. 8, 2015

(65) Prior Publication Data
US 2017/0115316 A1    Apr. 27, 2017

(30) Foreign Application Priority Data

Apr. 4, 2014  (JP) ................. 2014-077433

(51) Int. Cl.
*G01N 33/92* (2006.01)
*G01N 30/86* (2006.01)
*G01N 30/88* (2006.01)

(52) U.S. Cl.
CPC ......... *G01N 33/92* (2013.01); *G01N 30/8631* (2013.01); *G01N 30/88* (2013.01);
(Continued)

(58) Field of Classification Search
CPC ... G01N 2030/8822; G01N 2030/8831; G01N 30/86; G01N 30/8631; G01N 30/88; G01N 33/48; G01N 33/49; G01N 33/92
(Continued)

(56) References Cited

U.S. PATENT DOCUMENTS

| 8,268,626 | B2 | 9/2012 | Okazaki |
| 2008/0166745 | A1 | 7/2008 | Khan et al. |
| 2013/0289885 | A1* | 10/2013 | Otvos .................. G01N 33/92 |
| | | | 702/19 |

FOREIGN PATENT DOCUMENTS

| JP | 9-15225 A | 1/1997 |
| JP | 2002-139501 A | 5/2002 |

(Continued)

OTHER PUBLICATIONS

Gillett, M.P. Abstract from Annals of Saudi Medicine, vol. 21, No. 5-6, Sep.-Nov. 2001, pp. 283-286.*

(Continued)

*Primary Examiner* — Maureen Wallenhorst
(74) *Attorney, Agent, or Firm* — Seed IP Law Group LLP

(57) ABSTRACT

A concentration of cholesterol ester or free cholesterol can be calculated using the concentrations of total cholesterol and triglyceride in lipoproteins contained in a sample. Further, a concentration of lipoprotein particles in a fraction can be calculated using the lipoprotein particle size in the fraction. The concentrations of total cholesterol and triglyceride contained in a subject sample are detected. Using the concentrations of total cholesterol and triglyceride thus detected, the concentration of cholesterol ester or free cholesterol is calculated. Further, using the concentration of cholesterol ester or free cholesterol thus calculated, the concentration of lipoprotein particles in a fraction can be calculated.

5 Claims, 13 Drawing Sheets

(52) U.S. Cl.
CPC .............. *G01N 2030/8822* (2013.01); *G01N 2030/8831* (2013.01)

(58) Field of Classification Search
USPC .......................... 436/63, 71; 422/73; 435/11
See application file for complete search history.

(56) References Cited

FOREIGN PATENT DOCUMENTS

| | | |
|---|---|---|
| JP | 2005-80559 A | 3/2005 |
| JP | 2008-520993 A | 6/2008 |
| WO | 03/023397 A1 | 3/2003 |
| WO | 2006/057440 A1 | 6/2006 |

OTHER PUBLICATIONS

International Search Report for PCT/JP2015/060467, dated Jun. 23, 2015, 1 page.

Okazaki, M. et al., "Heterogeneity of Human Serum High Density Lipoproteins on High Performance Liquid Chromatography", J. Biochem., 1982; 92:517-524.

Yang, C. et al., "Structure of Apolipoprotein B-100 of Human Low Density Lipoproteins", Arteriosclerosis vol. 9, No. 1, Jan./Feb. 1989, pp. 96 to 108.

Schumaker, V. et al., "Apolipoprotein B and Low-Density Lipoprotein Structure: Implications for Biosynthesis of Triglyceride-rich Lipoproteins", Advances in Protein Chemistry 1994; 45: 205 to 248.

Segrest, J. et al., "The Amphipathic alpha Helix: A Multifunctional Structural Motif in Plasma Apolipoproteins", Advances in Protein Chemistry 1994; 45: 205 to 248.

McNamara, J. et al., "Differences in LDL subspecies involve alterations in lipid composition and conformational changes in apolipoprotein $B^1$", Journal of Lipid Research 1996; 37: 1924 to 1935.

Shinichi, U. et al., "A new on-line dual enzymatic method for simultaneous quantification of cholesterol and triglycerides in lipoproteins by HPLC", Journal of Lipid Research, vol. 43, p. 805-814, (2002).

International Search Report for EP Application No. 15772701.7 dated Aug. 23, 2017, 8 pgs.

\* cited by examiner

[Figure 1]
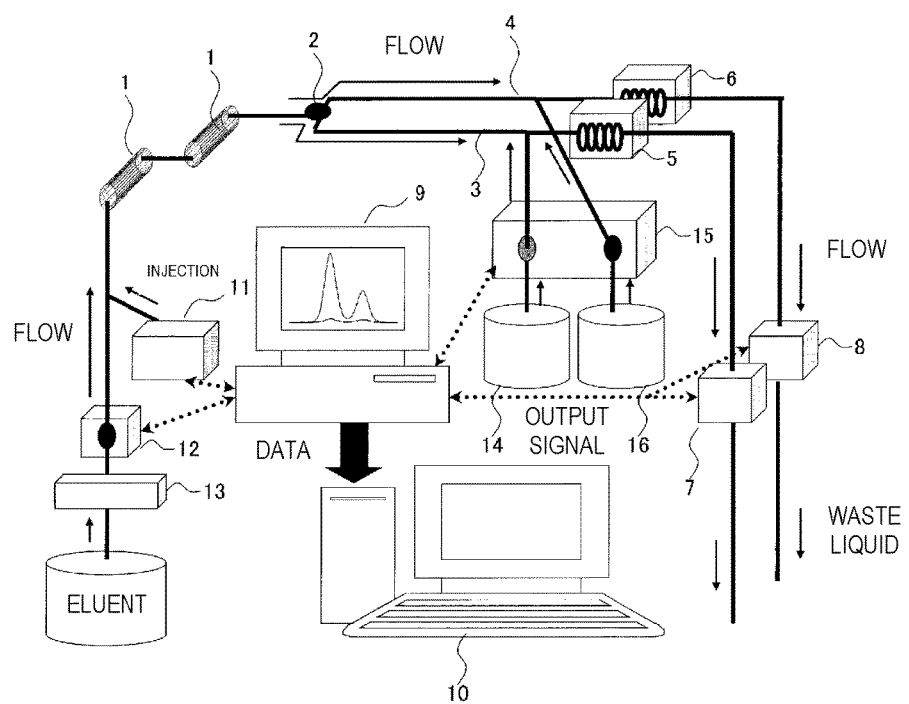

[Figure 2]
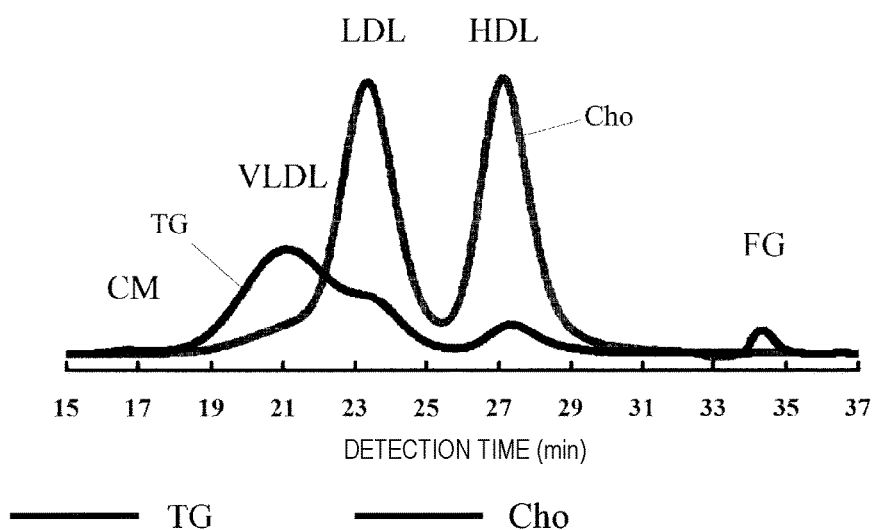

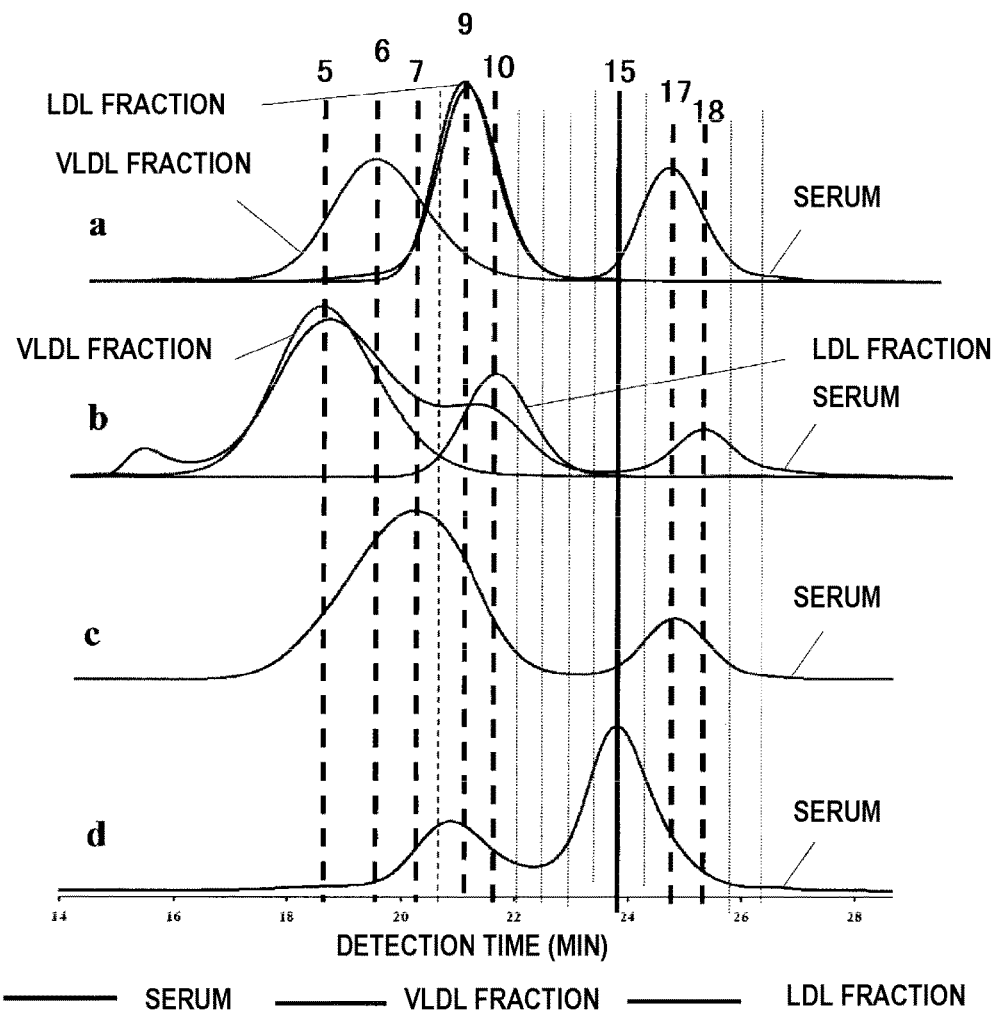
[Figure 3]

[Figure 4]
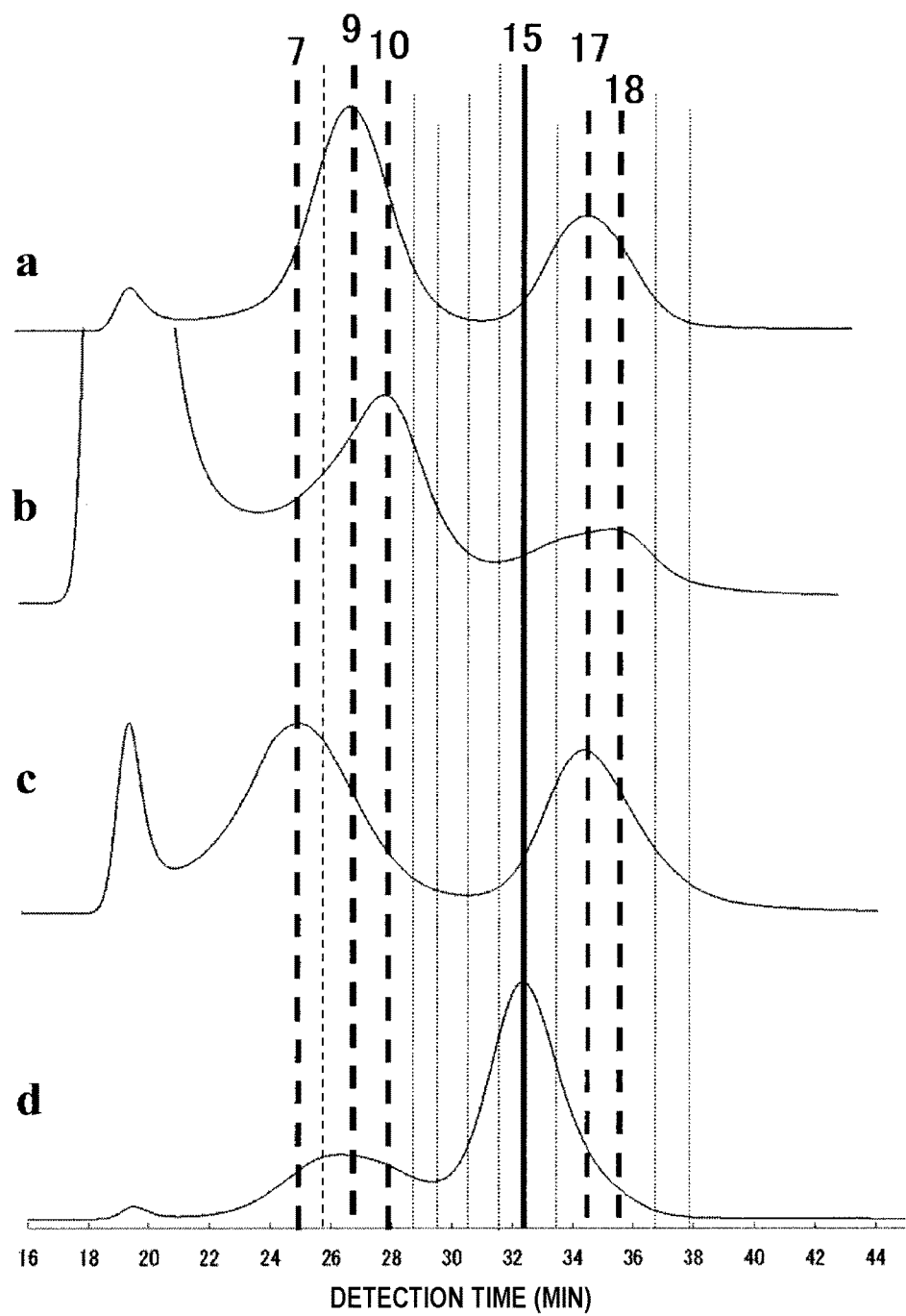

[Figure 5]
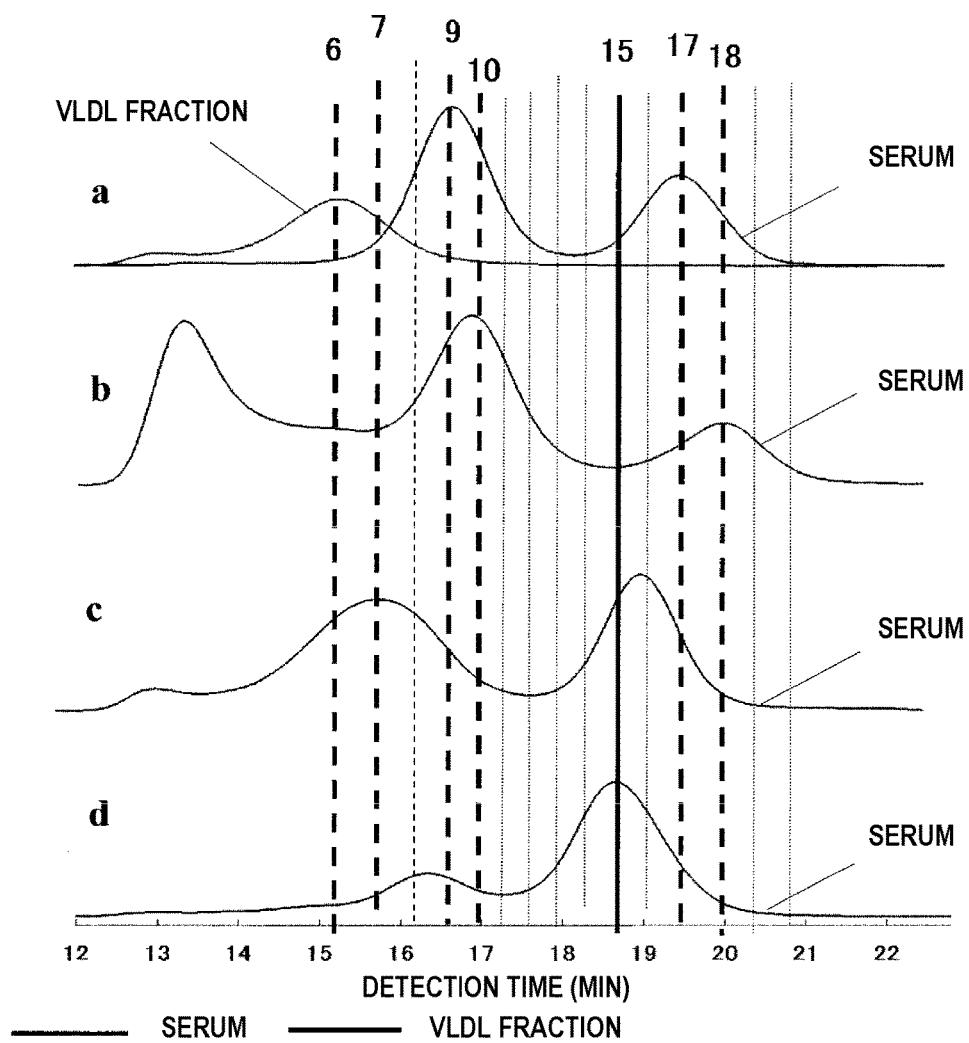

[Figure 6]
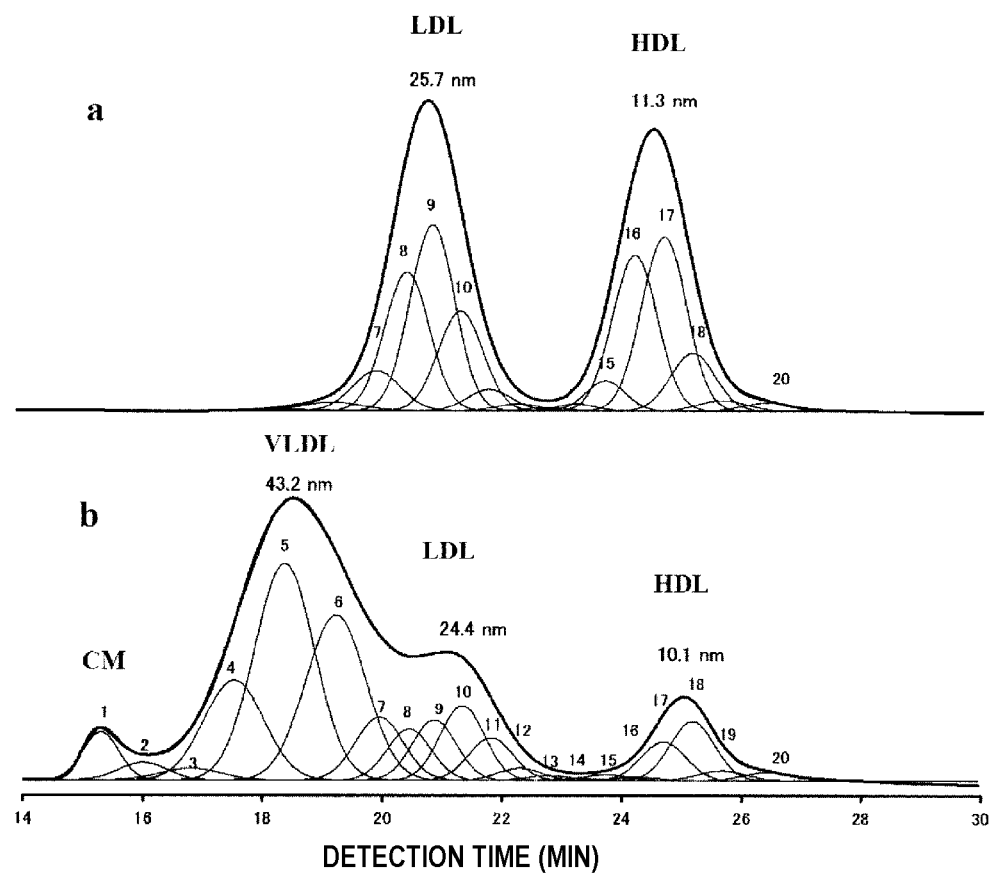

[Figure 7]
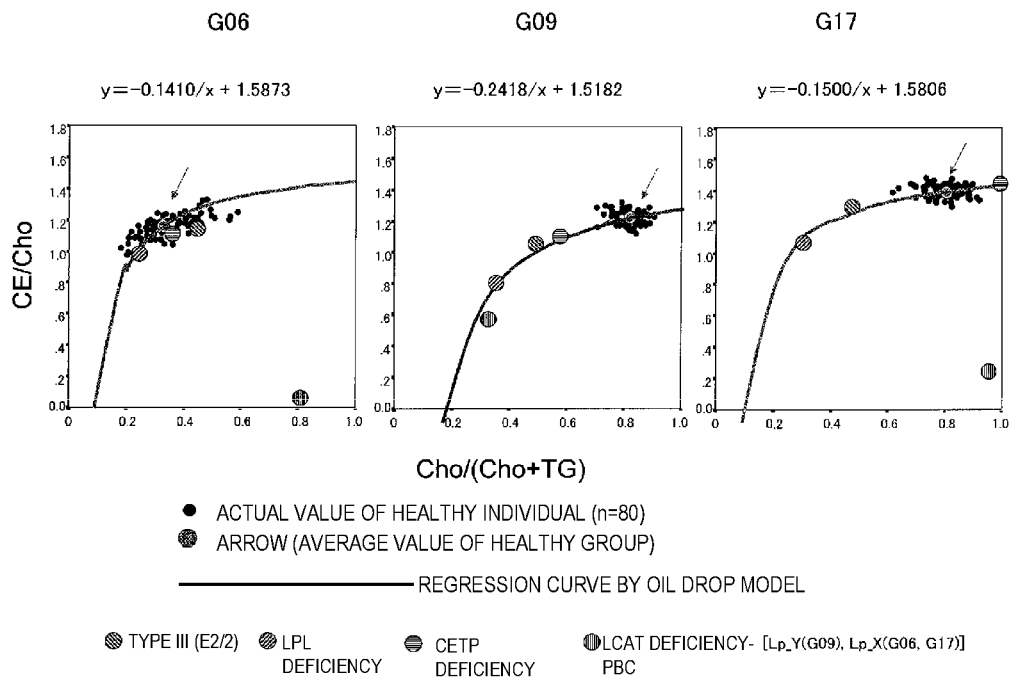
[Figure 8]
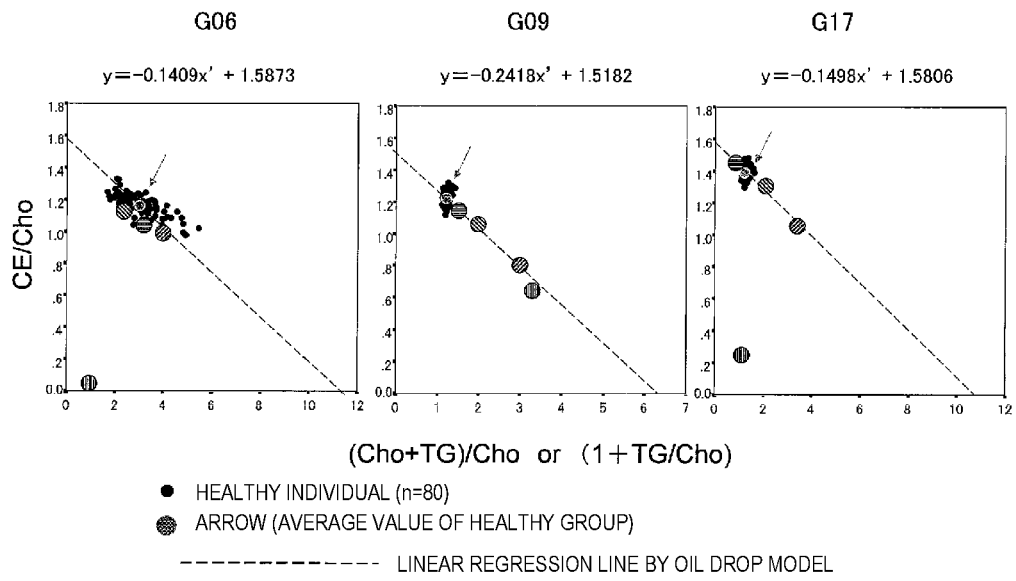

[Figure 9]
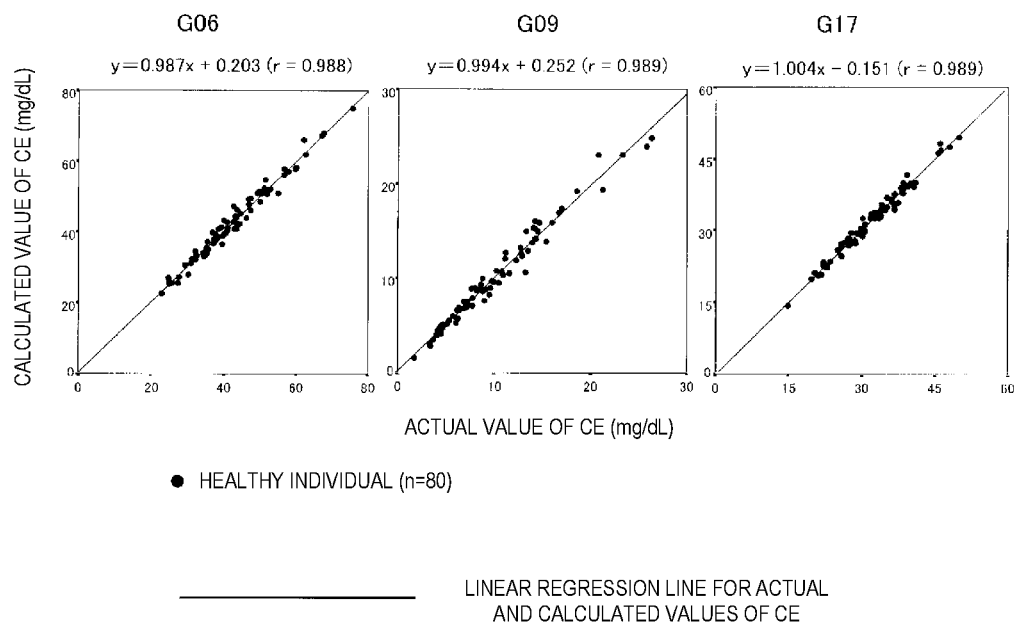

[Figure 10A]
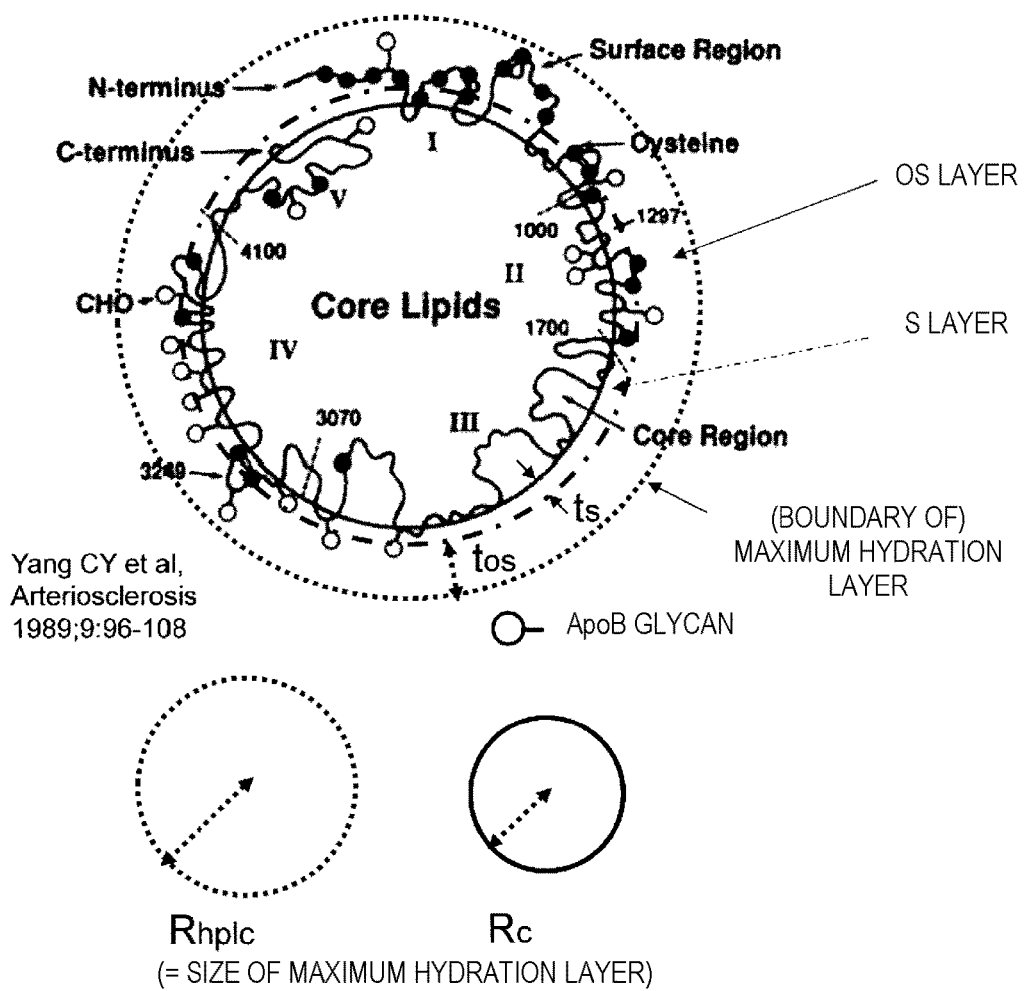

[Figure 10B]
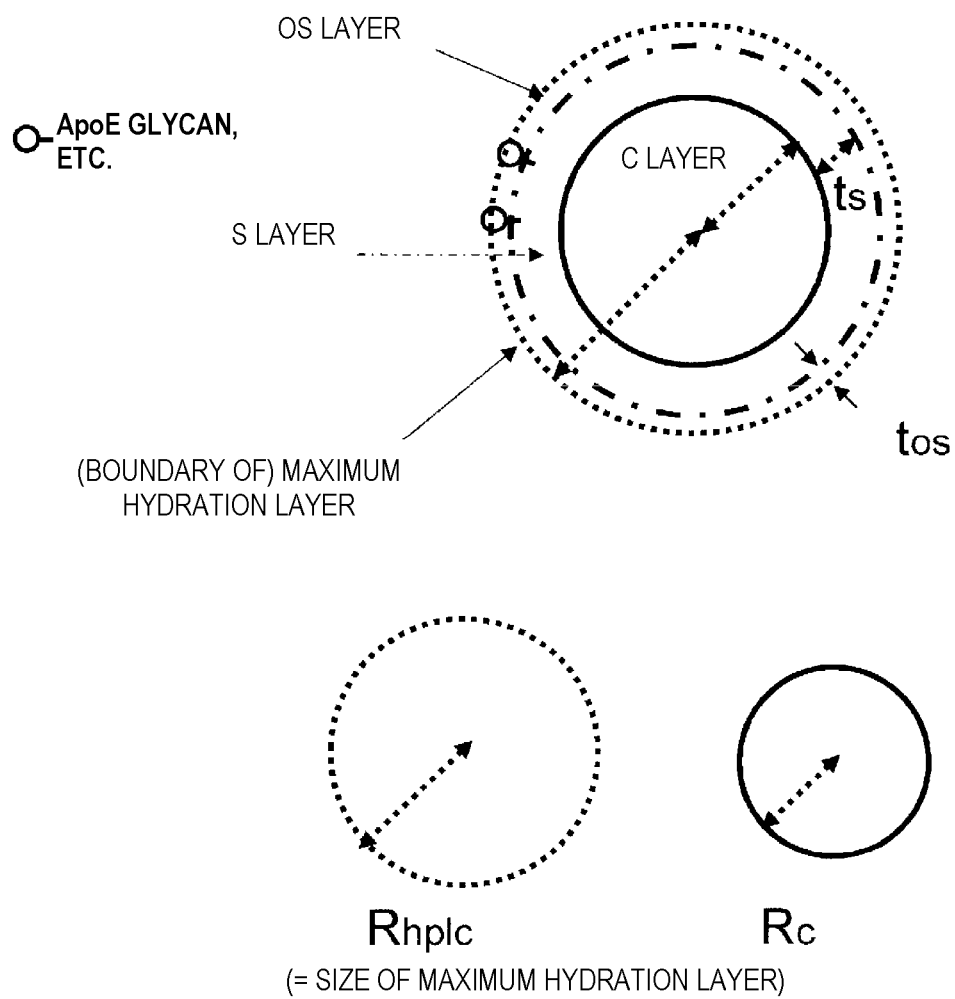

[Figure 11]
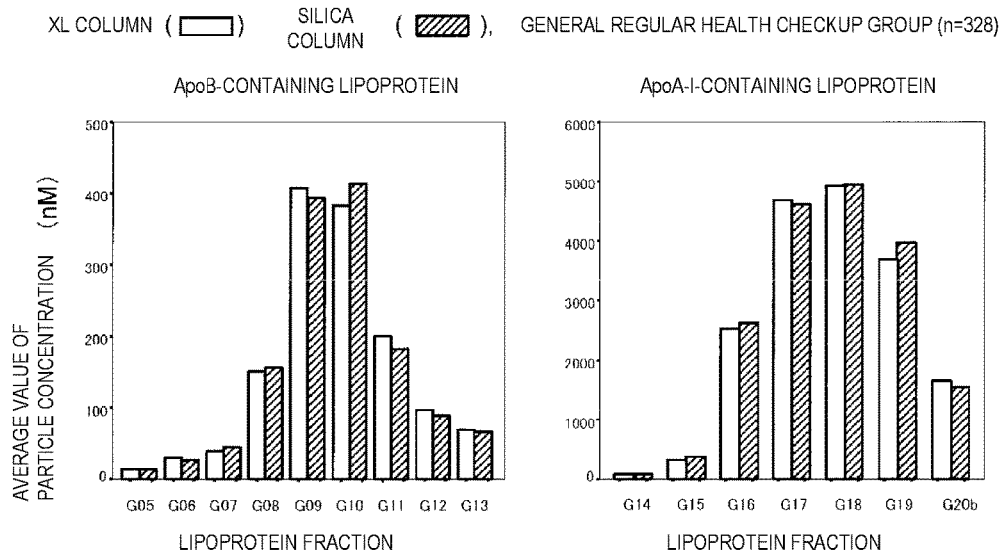
[Figure 12]
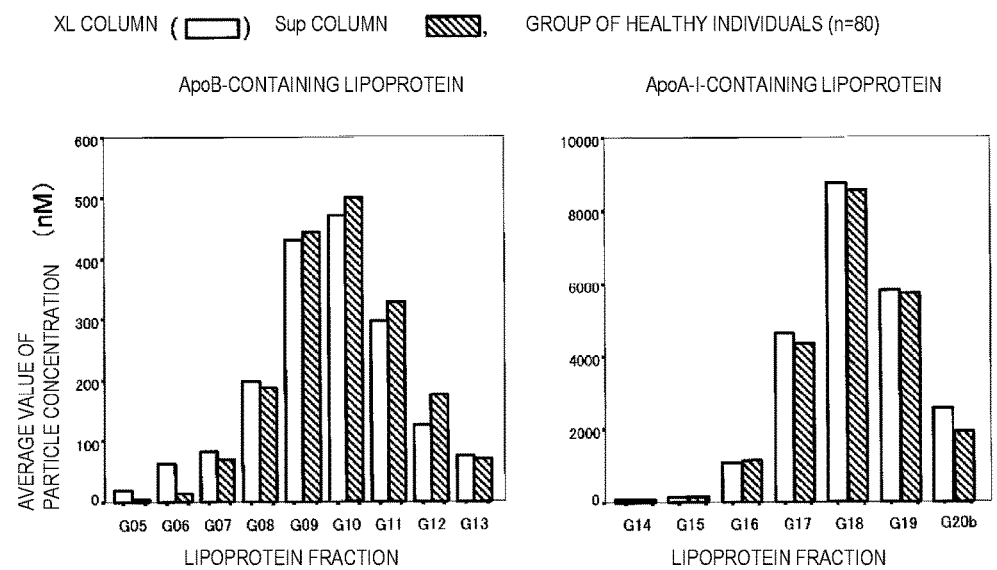

[Figure 13]
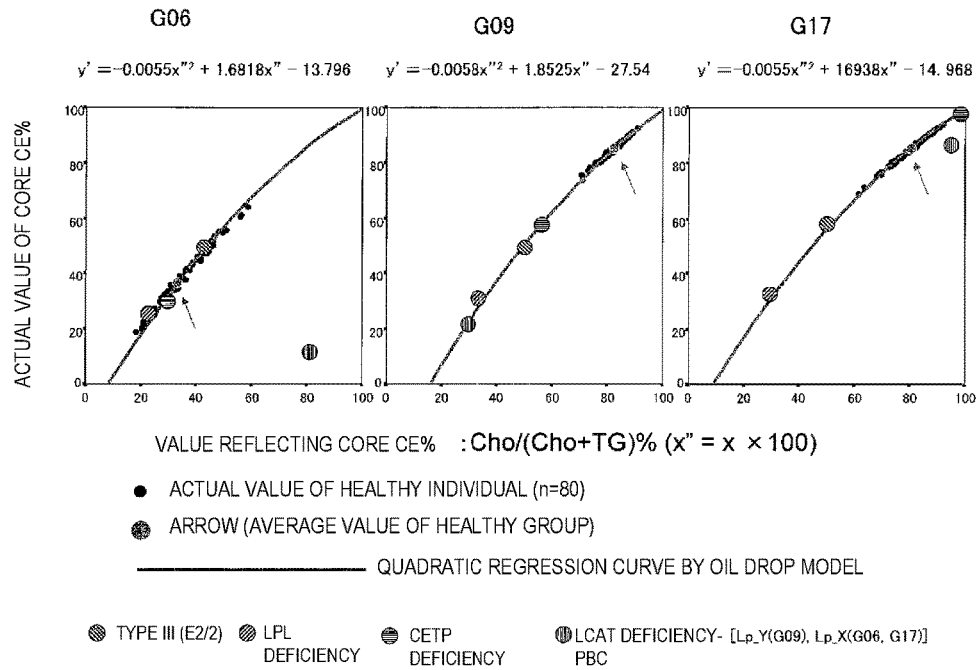
[Figure 14]
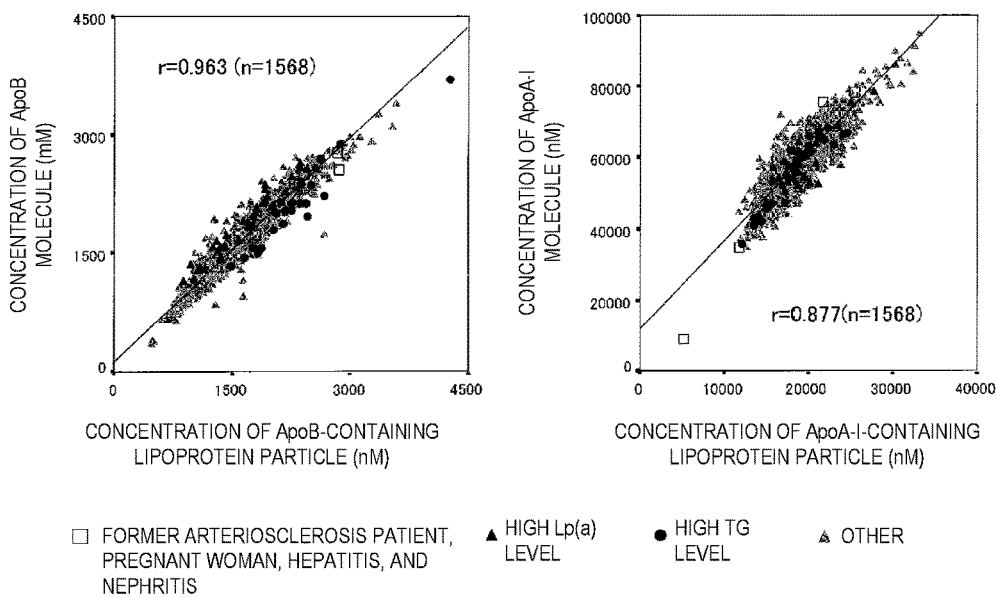

[Figure 15]
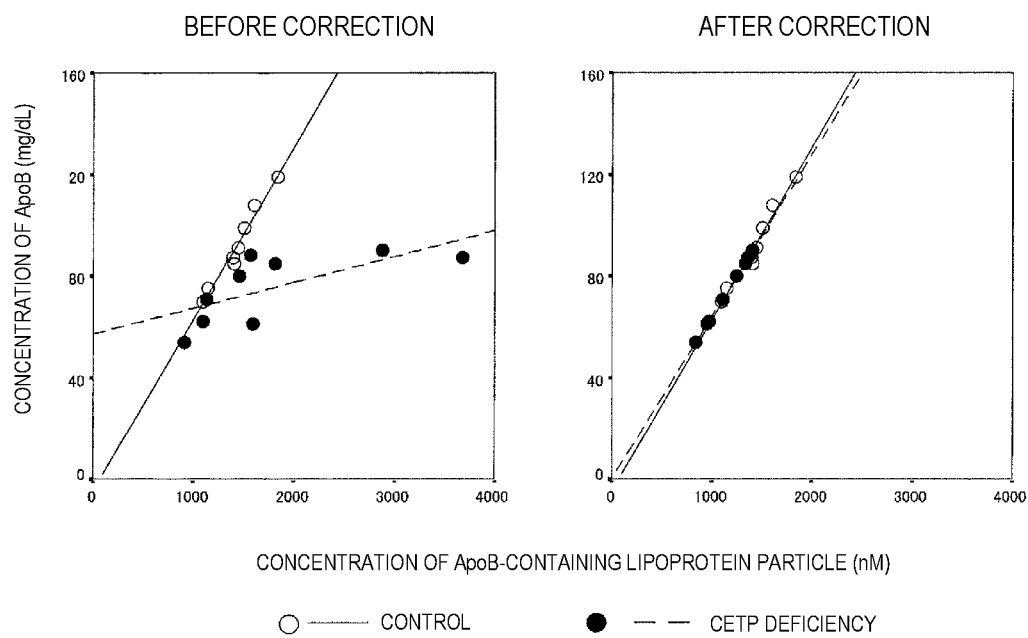
[Figure 16]
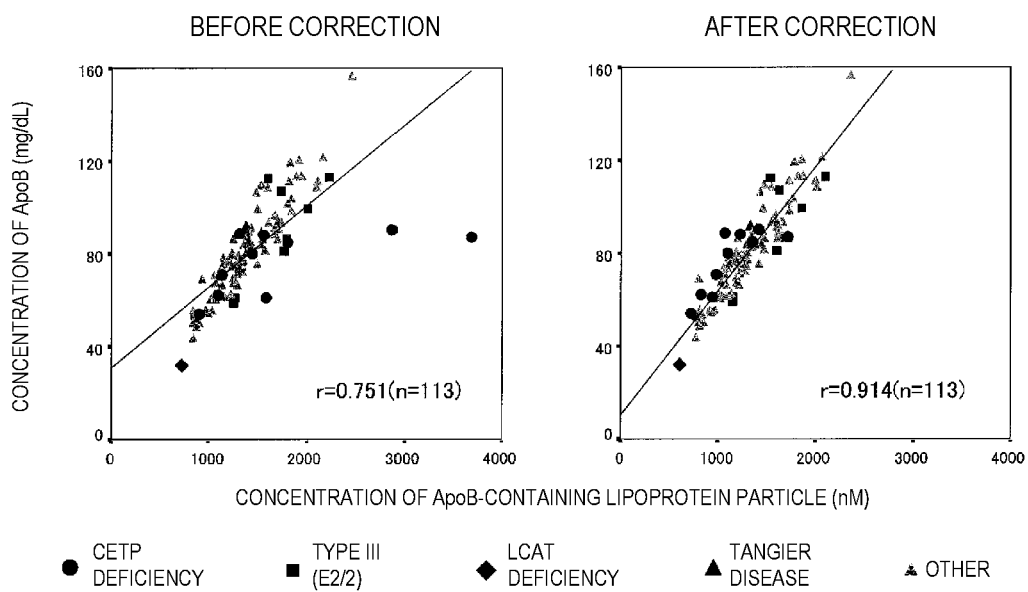

METHOD FOR ANALYZING LIPOPROTEINS

BACKGROUND

Technical Field

The present disclosure relates to a method for analyzing lipoproteins. Particularly, the present disclosure relates to a technique capable of calculating the concentration of cholesterol ester or free cholesterol, and further, the concentration of lipoprotein particles with high reliability from the actual measurement data obtained by analyzing lipoproteins.

Description of the Related Art

The following Patent Literature 1 describes a method for classifying lipoproteins contained in a subject sample according to the particle size by means of gel filtration liquid chromatography and then for quantifying cholesterol and triglyceride (triacylglycerol) being contained in the classified lipoproteins. According to this method, the lipoproteins are fractionated into chylomicrons, very low density lipoproteins, low density lipoproteins, and high density lipoproteins by subjecting the obtained chromatogram to waveform processing such as a Gaussian distribution curve approximation.

The following Patent Literature 2 discloses a method for classifying lipoproteins contained in a subject sample according to the particle size by means of gel filtration liquid chromatography and then for quantifying cholesterol and triglyceride being contained in the classified lipoproteins, wherein the lipoproteins are classified into 20 subclasses.

However, the classifying method disclosed in the Patent Literature 2 has been applied only to a case where a specific column is used, and respective peak positions for the 20 subclasses (i.e., particle size) have not been supported with theoretical foundation. For example, a particle size of LDL (low density lipoproteins) is determined to be 25.5 nm as a cutoff value when a GGE method (polyacrylamide density gradient gel electrophoresis) is used, and is determined to be about 20 nm based on a size observed by an electron microscope when a NMR method is used, and is determined to be 25.5 nm based on a size obtained by a GGE method when a gel filtration FPLC method is used, and is also determined to be 25.5 nm based on a latex bead or spherical proteins when a gel filtration HPLC is used. The particle size may vary depending on ways of estimation when a light scattering method is used. In addition, this particle size may become a different value by determining a molecular weight in accordance with equilibrium ultracentrifugation.

Therefore, definition of the lipoprotein subclasses based on the particle size and comparison of respective lipoproteins contained in a serum sample between these subclasses will lead to confusion.

In view of the foregoing circumstances, the present inventor made the following proposals in the following Patent Literature 3:

Use, as a reference, a peak position observed in a metabolic disorder patient whose lipoprotein metabolism suggests that the size ranges of VLDL, LDL, and HDL are narrow.

The use of the aforementioned reference peak position makes it possible to perform a comparison between the subclasses of a plurality of samples even if different gel filtration columns having different specifications of separation and molecular size range are used.

The above proposals made it possible to determine the component peaks of 20 subclasses independently of the type of a column.

CITATION LIST

Patent Literature

Patent Literature 1: Japanese Patent Laid-Open No. H9-15225

Patent Literature 2: Japanese Patent Laid-Open No. 2002-139501

Patent Literature 3: International Publication No. WO2006/057440

BRIEF SUMMARY

Technical Problem

It should be noted that the level of cholesterol as mentioned above refers to the concentration of total cholesterol (Cho). Cho is composed of cholesterol ester (CE), which is cholesterol linked to fatty acid, and free cholesterol (FC), which is cholesterol not linked to fatty acid. If the concentrations of CE or FC can be independently measured, it is expected to make a contribution to the determination of the disease state and the elucidation of the mechanism of action of a disease (such as arteriosclerosis).

However, conventionally, special procedures have been required to independently measure the concentrations of CE and FC, and this has been posing a problem of prolonging the measurement time and increasing the measurement cost.

Meanwhile, the present inventor obtained the following findings as a result of further research on the identification of lipoproteins:

There is a certain correlation between the concentrations of Cho and triglyceride (TG) and the concentration of CE in lipoproteins in a sample.

If the size of lipoprotein particles and the concentration of CE in a fraction can be obtained, then the concentration of lipoprotein particles in the fraction can be calculated.

The present disclosure was completed based on the above findings. As disclosed herein, the concentration of cholesterol ester or free cholesterol is calculated using the concentrations of total cholesterol and triglyceride in lipoproteins in a sample. As further disclosed herein, the concentration of lipoprotein particles in a fraction is calculated by further using the size of lipoprotein particles in the fraction.

Solution to Problem

Means to carry out the present disclosure can be described as shown in the following items.

(Item 1)

A method for analyzing lipoproteins, comprising the steps of: detecting concentrations of total cholesterol (Cho) and triglyceride (TG) in lipoproteins contained in a subject sample, and calculating a concentration of cholesterol ester (CE) or free cholesterol (FC) using the concentrations of Cho and TG.

(Item 2)

The method for analyzing lipoproteins according to Item 1, wherein the calculation of the concentration of CE is performed using a modeled relationship among the concentrations of Cho, TG, and CE or FC.

(Item 3)

The method for analyzing lipoproteins according to Item 2, wherein the modeled relationship is expressed by the following formula:

$$y = b_1/x + b_0 \quad (1)$$

wherein
x: Cho/(Cho+TG),
y: CE/Cho,
$b_1$: coefficient, and
$b_0$: constant.

In Item 3, the modeled relationship encompasses a relationship equivalent to formula (1).

(Item 4)

The method for analyzing lipoproteins according to Item 2, wherein the modeled relationship is expressed by the following formula:

$$y = b_1 x' + b_0 \quad (2)$$

wherein
x': (Cho+TG)/Cho,
y: CE/Cho,
$b_1$: coefficient, and
$b_0$: constant.

In Item 4, the modeled relationship encompasses a relationship equivalent to formula (2).

(Item 5)

The method for analyzing lipoproteins according to Item 2, wherein the modeled relationship is expressed by the following formula:

$$y' = b_2 x x''^2 + b_1' x x'' + b_0' \quad (5)$$

wherein
x'': Cho/(TG+Cho)×100,
y': CE/(TG+CE)×100,
$b_2$: coefficient,
$b_1'$: coefficient, and
$b_0'$: constant.

In Item 5, the modeled relationship encompasses a relationship equivalent to formula (5).

(Item 6)

The method for analyzing lipoproteins according to any one of Items 1 to 5,
wherein the detection of the concentration of Cho and the calculation of the concentration of CE or FC are carried out for each fraction defined based on a lipoprotein particle size.

(Item 7)

The method for analyzing lipoproteins according to any one of Items 1 to 6, further comprising the step of calculating a concentration of lipoprotein particles that contain the cholesterol ester (CE) therein,
wherein the calculation of the particle concentration is performed by tVc/standard Vc, wherein $$tVc = tVtg + tVce + tVfcc;$$

tVc: Sum of a core volume of all lipoproteins in a fraction of the subject sample;
tVtg: Sum of a volume of triglycerides in cores of all lipoproteins in the fraction;
tVce: Sum of a volume of cholesterol esters in cores of all lipoproteins in the fraction;
tVfcc: Sum of a volume of free cholesterols in cores of all lipoproteins in the fraction; and
Standard Vc: Volume of a core of one lipoprotein particle in the fraction.

(Item 8)

The method for analyzing lipoproteins according to Item 7, wherein the calculation of the particle concentration is carried out for each fraction defined based on a lipoprotein particle size.

(Item 9)

A lipoprotein analyzer, comprising
a detection unit for detecting concentrations of total cholesterol (Cho) and triglyceride (TG) in lipoproteins contained in a subject sample, and
a calculation unit for calculating a concentration of cholesterol ester (CE) or free cholesterol (FC) using the concentrations of Cho and TG.

(Item 10)

A computer program for executing the steps of the method for analyzing lipoproteins according to any one of Items 1 to 8 by a computer. The computer program may be contained in a non-transitory computer-readable medium and executed by the computer to carry out any one of Items 1 to 8.

Advantageous Effects

According to the present disclosure, the concentration of cholesterol ester or free cholesterol can be calculated using the concentrations of total cholesterol and triglyceride in lipoproteins in a sample. Also, according to the present disclosure, the concentration of lipoprotein particles in a fraction can be calculated by further using the lipoprotein particle size in the fraction.

BRIEF DESCRIPTION OF THE SEVERAL VIEWS OF THE DRAWINGS

FIG. 1 is a schematic diagram illustrating an example of a lipoprotein analyzer used in an embodiment of the present disclosure.

FIG. 2 is a chromatogram relating to Cho and TG, with a horizontal axis representing the detection time (min) and a vertical axis representing the detected value (mV).

FIG. 3 is an illustrative diagram comprised of FIGS. 3(a)-3(d) showing an example of data serving as a basis for defining, among twenty peaks consisting of G1 to G20, G5, G6, G7, G9, G10, G15, G17, and G18 as anchor peaks.

FIG. 4 is an illustrative diagram comprised of FIGS. 4(a)-4(d) showing an example of data obtained with a column different from that of FIG. 3.

FIG. 5 is an illustrative diagram comprised of FIGS. 5(a)-5(d) showing an example of data obtained with a column further different from that of FIG. 4.

FIG. 6 is a set of illustrative diagrams comprised of FIGS. 6(a) and 6(b) showing an example of analysis, in which a chromatogram is divided into twenty peaks by Gaussian approximation. FIG. 6(a) corresponds to the chromatogram of Cho in FIG. 2 and FIG. 6(b) corresponds to the chromatogram of TG in FIG. 2.

FIG. 7 is a set of illustrative diagrams showing a regression model, in which the actual Cho/(the actual TG+the actual Cho) is defined as x and the actual CE/Cho is defined as y.

FIG. 8 is a set of illustrative diagrams showing a regression model, in which (Cho+TG)/Cho or (1+TG/Cho) obtained with the actual values of Cho and TG is defined as x and CE/Cho obtained with the actual value of CE is defined as y.

FIG. 9 is a set of scatter plots, in which the value of CE calculated based on the regression model is defined as y and the actual value of CE is defined as x.

FIG. 10A is an illustrative diagram for explaining the oil drop model of spherical lipoproteins, showing a model of fractions G01 to G13.

FIG. 10B is an illustrative diagram for explaining the oil drop model of spherical lipoproteins, showing a model of fractions G14 to G20.

FIG. 11 is a set of illustrative diagrams comparatively showing the results of calculating the particle concentration by the method of the present embodiment using the actual values obtained using an XL column (TSKgel Lipopropak XL column) and a silica column (SkylightPak-LDL column) as the column of the lipoprotein analyzer.

FIG. 12 is a set of illustrative diagrams comparatively showing similar results to those shown in FIG. 11 as obtained with an XL column and a Sup column (Superose 6HR 10/30 column).

FIG. 13 is a set of illustrative diagrams showing a quadratic regression model, in which the actual Cho/(the actual TG+the actual Cho) % is defined as x" and the actual CE/(the actual TG+the actual CE) % is defined as y'.

FIG. 14 on the left is a graph showing the correlation between the actual concentration of apoB molecules and the calculated concentration of apoB-containing lipoprotein particles as obtained in the embodiment of the present disclosure. FIG. 14 on the right is a graph showing the correlation between the actual concentration of apoA-I molecules and the calculated concentration of apoA-I-containing lipoprotein particles as obtained in the embodiment of the present disclosure.

FIG. 15 is a set of graphs showing the correlation between the weight concentration of apoB and the concentration of apoB-containing lipoprotein particles in samples obtained from healthy individuals (control) and patients with CETP deficiency, before and after correction.

FIG. 16 is a set of graphs showing the correlation between the weight concentration of apoB and the concentration of apoB-containing lipoprotein particles in samples obtained from healthy individuals (control) and patients with CETP deficiency, before and after correction by another method of correction.

DETAILED DESCRIPTION

An embodiment of the present disclosure will now be described in detail with reference to the drawings.
(Configuration of a Lipoprotein Analyzer)

Firstly, as a premise of the description, an example of the lipoprotein analyzer used in the present embodiment will be described based on FIG. 1.

The analyzer comprises a column 1 for isolating a lipoprotein component contained in a subject sample, a splitter 2 for splitting an eluent buffer containing lipoprotein particles eluted from the column 1 into 2 portions, a first channel 3 and a second channel 4 both of which are split by the splitter 2, a total cholesterol (hereinafter, referred to as "Cho") reaction unit 5 placed on the first cannel 3, a triglycerides (hereinafter, referred to as "TG") reaction unit 6 placed on the second channel 4, a Cho detection unit 7 positioned downstream of the Cho reaction unit 5 on the first channel 3, a TG detection unit 8 positioned downstream of the TG reaction unit 6 on the second channel 4, a system controller 9 which acts so as to control the operation of this system and to which signals from the Cho detection unit 7 and the TG detection unit 8 are input, and an arithmetic unit 10 connected to the system controller 9, as shown in FIG. 1. The subject sample used herein is not specifically limited and refers to a liquid sample derived from an organism such as serum, plasma, a spinal fluid, a tissue fluid, or a lymph fluid, as well as a sample containing secretory particles derived from cell culture.

The analyzer of FIG. 1 also comprises a sampler 11 for supplying a serum sample to the column 1, a first pump 12 for supplying the eluent buffer to the column 1, and a degasser 13 for removing a gas from eluent buffer to be supplied to the column 1 by the first pump 12.

Although the column 1 used for the analyzer of FIG. 1 is not specifically limited, it is particularly preferable to use a column to which a filler for gel filtration is packed. In particular, an example of the column 1 may be a column packed with a filler whose average fine pore size is 800 to 1200 angstroms. When a filler whose average fine pore size is less than 800 angstrom is used, it is difficult to permeate lipoprotein particles having a large molecular size such as CM or VLDL into the fine pores. On the other hand, when a filler whose average fine pore size is more than 1200 angstrom is used, an ability thereof to isolate lipoprotein particles having a small molecular size such as LDL or HDL is reduced. Thus it is preferable to use a filler whose average fine pore size is 800 to 1200 angstroms as described above. Among others, a filler whose average fine pore size is 900 to 1100 angstroms is excellent in its isolation capacity, so that eventually allows for analysis of lipoproteins with high precision.

In addition, the filler is required to be selected so as to have a sufficient mechanical strength to withstand the application thereof to the liquid chromatography. Examples of such fillers include, for example, silica gel, polyvinyl alcohol, polyhydroxymetacrylate, and other materials based on hydrophilic resins (for example, TSKgel Lipopropak, trade name, produced by Tosoh Corp.).

Examples of the eluent buffers include phosphate buffer solutions, tris-buffer solutions, bis-tris buffer solutions and the like, but are not specifically limited thereto as long as the solution can isolate lipoprotein particles. Concentrations of the buffer solution is preferably within a range of 20 to 200 mM, and more preferably 50 to 100 mM, since a concentration of the buffer solution less than 20 mM is not sufficient to provide a suitable buffering capacity and a concentration more than 200 mM may inhibit a reaction between the an enzyme reagent described below and Cho or TG. A pH value of the buffer solution is 5 to 9, and more preferably 7 to 8, since the pH value less than 5 or more than 9 may inhibit the reaction with the enzyme reagent as described above. However, the pH value is not limited thereto as long as the measurement of the Cho and/or TG is performed without the enzyme.

The Cho reaction unit 5 is connected via the second pump 15 to a Cho reagent reservoir 14 containing a reagent which is used for quantifying Cho included in an eluent buffer having lipoprotein particles eluted from the column 1. Examples of the reagents for quantifying Cho include, but not specifically limited to, an enzyme-dye reagent obtained by combining an enzyme such as cholesterol esterase, cholesterol oxidase, or peroxidase with a dye such as N-ethyl-N-(3-methylphenyl)-N'-succinylethylenediamine, 4-amino-antipyrin, or N-ethyl-N-(3-sulfopropyl)-m-anisidine, for example. Examples of such reagents which can preferably be used are commercially available determiner L TCII (Kyowa Medex Co., Ltd.) and type L CHO.H (Wako Pure Chemical Industries Ltd.) principal upstream cause. These reagents react with Cho to provide reaction products having absorbing or fluorescing characteristics which are detectable by a spectroscope such as a fluorescence detector or a ultraviolet-visible light detector.

The TG reaction unit 6 is connected via the second pump 15 to a TG reagent tank 16 containing a reagent which is used for quantifying TG included in an eluent buffer having lipoprotein particles eluted from the column 1. Examples of the reagents for quantifying TG include, but not specifically limited to, an enzyme-dye reagent obtained by combining an enzyme such as ascorbate oxidase, glycerol kinase, glycerol-triphosphate oxidase, lipoprotein lipase, and peroxydase with a dye such as quinone-based chromophoric dye, for example. Examples of the quinone-based chromophoric dyes include an oxidative condensate of N-ethyl-N-(3-methylphenyl)-N'-succinylethylenediamine or N-ethyl-N-(3-sulfopropyl)-m-anisidine and 4-antiaminopyridine. Examples of such reagents which can preferably be used are commercially available determiner L TGII (Kyowa Medex Co., Ltd.) and type L TGH (Wako Pure Chemical Industries Ltd.).

Each of the Cho reaction unit 5 and the TG reaction unit 6 is provided with a reaction coil for controlling a temperature during the reaction of the above described reagent with Cho or TG. A reaction temperature of the above described reagent and Cho or TG in the reaction unit 5 or the reaction unit 6 is 35 to 50° C., and preferably 45 to 50° C., since the reaction temperature less than 35° C. may be insufficient to carry out the reaction and the reaction temperature more than 50° C. may result in the deterioration of the enzyme during the reaction thereof.

The Cho detection unit 7 is provided with, for example, an ultraviolet-visible light detector for detecting an absorbance of the reaction product produced by the reaction between Cho and the reagent in the Cho reaction unit 5. The TG detection unit 8 is provided with, for example, an ultraviolet-visible light detector for detecting an absorbance of the reaction product produced by the reaction between TG and the reagent in the TG reaction unit 6. For example, when a quinone-based chromophoric dye is used as the above described reagent, a measurement wave length of the ultraviolet-visible light detector may be 540 to 560 nm.

The system controller 9, to which output signals from the Cho detection unit 7 and the TG detection unit 8 are input, has the function of outputting a Cho chromatogram and a TG chromatogram as a result. A chromatogram output from the system controller 9, with a horizontal axis representing an elution time (min.) and a vertical axis representing a detected value (mV), can display a Cho chromatogram with a TG chromatogram superimposed thereon as shown in FIG. 2, for example.

As the arithmetic unit 10, it is possible to use a computer on which an analytical program as described below is installed, for example, using a non-transitory computer-readable medium. The arithmetic unit 10 is connected to the system controller 9, and has functions of carrying out data processing on the chromatogram being output from the system controller 9 by the use of the analytical program, separating lipoprotein particles contained within the subject sample into twenty component peaks, and calculating amounts of Cho and TG. The arithmetic unit 10 may also be connected to the system controller 9 via an information communication circuit network such as the Internet, LAN, or an intranet.

(Operation of Lipoprotein Analyzer)

According to the above described lipoprotein analyzer, various lipoproteins are firstly classified depending on the particle size thereof through the column 1, and then Cho and TG which are contained in the eluent buffers eluted from the column 1 are quantified. Therefore, the lipoprotein analyzer is able to quantify Cho and TG for every subclass of lipoproteins depending on a resolution of the column 1.

The lipoproteins are classified into a plurality of classes based on differences in the properties such as particle size, hydration density, degrees of electrophoresis and the like. The present analyzer separates lipoprotein particles included in the serum sample into twenty component peaks in accordance with the analytical program as described below.

Now the analytical program will be described. The analytical program controls the arithmetic unit 10 following a flowchart comprising Step 1 and Step 2.

(First Step for Analyzing)

Step 1 is to firstly input a chromatogram as an input signal which is output from the system controller 9 via input means of the arithmetic unit 10. That is, the analytical program executes the computer as detection means for input a chromatogram as an input signal which is output from the system controller 9 at Step 1.

Step 1 will now be described in detail. Firstly, a Cho chromatogram and a TG chromatogram as shown in FIG. 2 are input via input means of the arithmetic unit 10, and then the chromatograms and/or numeric data supporting the chromatograms are stored in an intrinsic memory of the arithmetic unit 10 or recorded on a recording medium which is recordable by the arithmetic unit 10.

(Second Step for Analyzing)

Next, Step 2 is to perform data processing of the input chromatograms and then to classify the obtained results into twenty component peaks in order to calculate the Gaussian approximated curves. That is, execution of the analytical program causes the computer to act as data processing means for calculating the Gaussian approximated curves at Step 2. The data processing means allows for separation of the chromatogram which is input at Step 1 into independent twenty peaks. In the following description, the independent twenty peaks are referred to as G1 to G20 in decreasing order of size. G1 and G2 are component peaks corresponding to chylomicrons (CM), G3 to G7 are component peaks corresponding to very low density (specific gravity) lipoproteins (VLDL), G8 to G13 are component peaks corresponding to low density lipoproteins (LDL), and G14 to G20 are component peaks corresponding to high density lipoproteins (HDL). Among component peaks corresponding to VLDL, G3 to G5 indicate large VLDL, G6 indicates medium VLDL, and G7 indicates small VLDL. Among component peaks corresponding to LDL, G8 indicates large LDL, G9 indicates medium LDL, G10 indicates small LDL, and G11 to G13 indicate very small LDL. Among component peaks corresponding to HDL, G14 and G15 indicate very large HDL, G16 indicates large HDL, G17 indicates medium HDL, G18 indicates small HDL, and G19 and G20 indicate very small HDL.

The data processing means at Step 2 is to separate or classify the chromatogram or numeric data which are input at Step 1 into twenty component peaks and then to allow the arithmetic unit 10 to perform calculations of the Gaussian approximated curves including G1 to G20. The twenty component peaks are those being separated in accordance with the size of lipoprotein particles.

Respective peak positions of respective twenty component peaks are defines as described below. As for the respective twenty peaks comprising G1 to G20, peak positions (elution times) of standard peaks (anchor peaks) are firstly determined, and then peak positions of peaks other than the anchor peaks (extra essential peaks) are determined. Specifically, G5, G6, G7, G9, G10, G15, G17, and G18 are defined as anchor peaks and G1 to G4, G8, G11 to G14, G16, G19, and G20 are defined as extra essential peaks by way of examples. FIG. 3 shows an example of data which support the definition of G5, G6, G7, G9, G10, G15, G17, and G18 as anchor peaks.

(Determination of Anchor Peaks)

Since particles of VLDL size, LDL size, and HDL size in the mormolipidemic middle-aged men (age 30s to 40s) population are respectively distributed in certain ranges, each of elution positions thereof is determined to be at G6, G9, and G17 among these anchor peaks (see FIG. 3(a)). Specifically, Cho chromatograms and TG chromatograms as shown in FIG. 2 are obtained from serum samples which have been collected from a plurality of mormolipidemic middle-aged men (age 30s to 40s). On the obtained chromatograms, peaks corresponding to major categories VLDL, LDL, and HDL are appeared in this order. An average value of the peak position corresponding to each of VLDL, LDL, and HDL on the chromatograms obtained from the plurality of mormolipidemic middle-aged men is calculated, and the average VLDL size, average LDL size, and average HDL size are defined as elution positions at G6, G9, and G17 respectively.

In the case where a lipoprotein lipase activity is absent or very low, triglycerides of the TG-rich lipoprotein is not decomposed, and VLDL still having a large size remains in blood. Therefore, particles of the VLDL size in the case where the lipoprotein activity is absent or very low are significantly larger than those of the mormolipidemic men, and are distributed within a certain size range. An average elution position of the VLDL is defined as an elution position of G5 among the anchor peaks (see FIG. 3(b)).

In addition, following the function of cholesterol ester transfer protein presenting in blood, triglycerides are transferred from VLDL to LDL while cholesterol esters are transferred from LDL to VLDL. LDL becomes triglyceride-rich particles, and triglycerides in LDL are decomposed by hepatic lipase and LDL becomes smaller. Particle sizes of LDL in the case where a lipoprotein lipase activity is absent or very low are significantly smaller than a LDL size of the mormolipidemic men, and are distributed within a certain size range. Thus, an average elution position of this LDL is defined as an elution position of G10 among the anchor peaks (FIG. 3(b)).

In addition, in the case where the lipoprotein lipase activity is absent or very low, triglycerides are transferred from LDL or VLDL to HDL while cholesterol esters are transferred from LDL to LDL or VLDL. Consequently, HDL becomes rich in triglycerides, and triglycerides in HDL are decomposed by hepatic lipase and thus the HDL becomes smaller. Therefore, particles of HDL size in the case where the lipoprotein lipase activity is absent or very low are significantly smaller than those of the mormolipidemic men, and are distributed within a certain range. Thus, an average elution position of this HDL is defined as an elution position of G18 among anchor positions (see FIG. 3(b)).

Still further, in the case suffering from cholesterol ester transfer protein deficiency, cholesterol esters are not transferred from HDL to LDL or VLDL while triglycerides are not accepted from LDL or VLDL, so that HDL becomes rich in cholesterol and also becomes larger in size. Especially in the cholesterol ester transfer protein deficiency, HDL includes little triglycerides. Particles of HDL size in the case where the cholesterol ester transfer protein is completely deficient are significantly larger than those of the mormolipidemic men, and are distributed within a certain size range. Thus an average elution position of this HDL is defined as an elution position of G15 among anchor peaks (see FIG. 3(d)).

Still further, in the type III hyperlipidemia with ApoE2/2, substitution of Cys for Arg at the 158th position results in conformational variation of a site binding to LDL receptors (ApoB/E), LDL receptor associated proteins, and VLDL receptors which have ApoE as ligands, so that incorporation of small VLDL (remnant) is reduced, components corresponding to the small VLDL are increased in blood, and consequently specific peaks are observed. Thus, an average elution position of the VLDL in this case is defined as an elution position of G7 among anchor peaks (see FIG. 3(c)). The elution position of the small VLDL is corresponding to that of intermediate density lipoproteins (IDL) isolated by ultracentrifugation as a fraction with density between 1.006 g/ml and 1.019 g/ml from a plurality of human subjects including type III hyperlipidemia with apo E2/2 (see Shinichi Usui, Yukichi Hara, Seijin Hosaki, and Mitsuyo Okazaki, Journal of Lipid Research, Volume 43, p 805-814, (2002)). Further, the cholesterol content in the IDL fraction highly correlates to the cholesterol content in the small VLDL in the present disclosure. Therefore, the small VLDL determined by anchor peak G7, which is remarkably increased in the type III hyperlpidemia with apo E2/2 corresponds to remnant lipoproteins and/or IDL.

Although the data shown in FIG. 3 are obtained by using two TSKgel LipopropakXL columns (produced by Tosoh Corp.), data obtained by using other columns may also be used as data which support the definition as the anchor peaks.

For example, data can be similarly obtained by using a Superose 61R 10/30 column (produced by Pharmacia) as shown in FIG. 4, and thus anchor peaks can be defined based on these data. In this case, elution positions of G9 and G17 can be defined from a profile of mormolipidemic middle-aged men (age 30s to 40s) (FIG. 4(a)). Elution positions of G10 and G18 can be defined from a profile of a case where the lipoprotein lipase activity is absent or very low (FIG. 4(b)). An elution position of G7 can be defined from a profile of a case of the type III hyperlipidemia with ApoE2/2 (FIG. 4(c)). An elution position of G15 can be defined from a profile of a case where the cholesterol ester transfer protein is completely deficient (FIG. 4(d)).

For further example, data can be similarly obtained by using a SkylightPak-LDL column (produced by Skylight Biotech Inc.) as shown in FIG. 5, and thus anchor peaks can be defined based on these data. In this case, elution positions of G6, G9 and G17 can be defined from a profile of mormolipidemic middle-aged men (age 30s to 40s) (FIG. 5(a)). Elution positions of G10 and G18 can be defined from a profile of a case where the lipoprotein lipase activity is absent or very low (FIG. 5(b)). An elution position of G7 can be defined from a profile of a case of the type III hyperlipidemia with ApoE2/2 (FIG. 5(c)). An elution position of G15 can be defined from a profile of a case where the cholesterol ester transfer protein is completely deficient (FIG. 5(d)).

As described above, respective elution positions are defined provided that G5, G6, G7, G9, G10, G15, G17, and G18 are anchor peaks.

(Determination of Extra Essential Peaks)

Next, as for extra essential peaks, positions and widths of the peaks are mathematically determined. The extra essential peaks are necessary for analyzing component peaks by Gaussian approximation in which the size and distribution of the component peaks are fixed (time and width are fixed). In terms of LDL and HDL, a distribution width of component peaks comprising anchor peaks and extra essential peaks is assumed to be almost the same to each other, and extra essential peaks are also assumed to be located between the anchor peaks at almost equal intervals. Four extra essential peaks (peaks 11 to 14) are set between G10 and G15, one extra essential peak (peak 8) is set between G7 and G9, one extra essential peak (peak 16) is set between G15 and G17, and two extra essential peaks (peaks 19 and 20) are set after G18. Positions of extra essential peaks (peaks 16 to 20) belonging to HDL can be defined with reference to correspondence between the peak observation frequencies in the normal population and the experimental values obtained by performing re-chromatography, in the analysis which uses another HDL-specific column (see Okazaki M et al., J. Biochem., 1982; 92:517-524).

Positions of component peaks G8 to G20 were determined to be at almost equal intervals and widths thereof were also determined to be almost equal. Component peaks 2, 3, 4 were necessary to perform Gaussian approximation between a peak 1 at Void and G5 of an anchor peak, and were determined in accordance with a rule between the peak intervals and the widths.

In addition, a minimum value of the component peak widths can be defined as a free glycerol (particle whose molecular weight is 92 and whose size is homogeneous, FG as presented in FIG. 2) width obtained from the analytical system, and a maximum value thereof can be defined as two times as large as an interval between adjacent component peaks.

As for twenty component peaks, the peak width can be set to a numeric value obtained by the following equation, SD (min.)=half width of peak (sec.)/143. Specifically, values as described below are input or preset as the peak widths of twenty component peaks: 033 min. for G01; 0.40 min. for G02; 0.55 min. for G03; 0.55 min. for G04; 0.55 min. for G05; 0.50 min. for G06; 0.40 min. for G07; 0.38 min. for G08; 0.38 min. for G09; 0.38 min. for G10; 0.38 min. for G11; 0.38 min. for G12; 0.38 min. for G13; 0.38 min. for G14; 0.38 min. for G15; 0.38 min. for G16; 0.38 min. for G17; 0.38 min. for G18; 0.38 min. for G19; and 0.48 min. for G20.

The data processing means at Step 2 can be carried out by applying a Gaussian curve fitting computation algorithm, for example. According to the Gaussian curve fitting computation algorithm, twenty component peaks can be obtained as described below.

That is, firstly, given that a single peak on a chromatogram takes a form of a symmetric Gaussian distribution, a peak height h(t) at a time t can be expressed as $$h(t)=H\times\exp(-(t-T)^2/2\sigma^2)$$

where T is a position of a peak and σ is a width (standard deviation) (H is a maximum value of the peak heights). It is known that the peak also takes a form of (1) Peason VII, (2) Lorentzian, (3) exponentially modified Gaussian, (4) Weibull, (5) bi-Gaussian, (6) poisson, (7) Gram-Charlier, (8) combination of Gauss and Cauchy functions, (9) combination of statistical moments, or (10) cam-driven analog peak, so that it is possible to assume that the peak takes a form of any of these (1) to (8).

A height of the $n^{th}$ peak, hn(t), can be expressed as $$hn(t)=Hn\times\exp(-(t-Tn)^2/2\sigma n^2) \quad \text{I}$$

where Tn is a position of the $n^{th}$ peak and σn is a width (standard deviation) (Hn is a maximum value of the $n^{th}$ peak (height)).

Given that $\exp(-(t-Tn)^2/2\sigma n^2)=Gn(t)$, a formula I can be expressed as $$hn(t)=Hn\times Gn(t) \quad \text{II.}$$

Given that N peaks are respectively independent, a synthetic curve at a time t A(t) is expressed as $$A(t)=h1(t)+h2(t)+\ldots+hn-1(t)+hn(t)=H1\times G1(t)+H2\times G2(t)+\ldots+Hn-1\times Gn-1(t)+Hn\times Gn(t). \quad \text{III}$$

Given that the number of data points is m, the above described formula III can be expressed as follows in m different ways:

$$A(t1)=H1\times G1(t1)+H2\times G2(t1)+\ldots+Hn-1\times Gn-1(t1)+Hn\times Gn(t1);$$

$$A(t2)=H1\times G1(t2)+H2\times G2(t2)+\ldots+Hn-1\times Gn-1(t2)+Hn\times Gn(t2);$$

... ; and $$A(tm)=H1\times G1(tm)+H2\times G2(tm)+\ldots+Hn-1\times Gn\times 1(tm)+Hn\times Gn(tm).$$

Given that an actual curve of an chromatogram at a time t is indicated by R(t), a curve fitting method is used for determining the peak numbers n, peak positions T, and widths (standard deviations) σ so as to obtain R(t)=A(t). Practically, since a formula R(t)=A(t) can not be achieved at any time by a linear method of least squares, parameters by which the sum of $(R(t)-A(t))^2$ becomes minimum are determined.

In addition to the curve fitting method, it is also possible to apply an iterative method (such as Fletcher Powell, Marquardt, Newton-Raphson, Simplex minimization, Box-Complex method) for example. However, these procedures other than the curve fitting method have disadvantages as follows, that is: an initial value has an effect on the calculation result; it is necessary to assume previously whether the curve corresponds to Gaussian or to Lorentzian; and convergence is difficult to achieve when the number of peaks are larger (4 or more). Therefore, it is very important to know how to determine an initial value which is closer to a true value. Procedures such as (1) factor analysis, (2) moments analysis, (3) orthogonal polynominal analysis, and (4) inverse diffusion model have recently been reported as a peak separation method for overcoming these disadvantages; and can also be applied to the present algorithm.

Since ti (i=1, 2, ..., m) is a constant, any Gn (ti) also becomes a constant. Thus, the above described formula III can be expressed as follows in m different ways;

$$A(t1)=H1\times G1(t1)+H2\times G2(t1)+\ldots+H19\times Gn-1(t1)+H20\times G20(t1);$$

$$A(t2)=H1\times G1(t2)+H2\times G2(t2)+\ldots+H19\times Gn-1(t2)+H20\times G20(t2);$$

... ; and $$A(tm)=H1\times G1(tm)+H2\times G2(tm)+\ldots+H19\times G19(tm)+H20\times G20(tm).$$

Given that R(t)=A(t), m primary expressions each of which comprises 20 unknown numbers H1, H2, ..., H19, and H20 can be obtained. If m=20, then a solution can be found by solving the primary expression.

Although the number of data points is not 20 in the actual data, 20 points at which calculation is easily carried out at high speed (for example, twenty peak positions each of which exist in respective twenty component peaks) are conveniently selected for calculation in the present algorithm. In the present algorithm, the number of data points may not be selected to be 20 points but may determined by a method of least squares.

According to the flowchart comprising Step 1 and Step 2 as described above, a chromatogram which is output from the system controller 9 (for example, a chromatogram shown in FIG. 2) can be separated into twenty component peaks. A profile obtained by the separation into twenty component peaks, which shows a noticeable correlation with visceral fat area (VFA), is effectively utilized for examining the risk of diseases caused by accumulation of visceral fat.

Examples of diseases caused by the accumulation of visceral fat include arteriosclerotic diseases represented by an ischemic heart disease, for example. That is, as a result of over-nutrition or low physical activity associated with recent changes in life-style which leads to fat accumulation and obesity, the incidence of arteriosclerotic diseases represented by an ischemic heart disease have been increased due to the accumulation of numerous risk factors. This kind of disease is developed by inducing an insulin resistance due to a hereditary predisposition causing the insulin resistance combined with an acquired factor such as obesity. It is important to consider intra-abdominal visceral fat accumulation as a principal upstream cause. The intra-abdominal accumulation of visceral fat caused by obese people as well as by not-obese people closely contributes to the onset of diabetes, hypertension, and coronary artery disease (CAD). Thus, examples of diseases caused by the accumulation of visceral fat include diabetes, hypertension, hyperlipidemia, and coronary artery disease.

(Assumption of the Oil Drop Model in the Present Embodiment)

Based on the explanation given above, an "oil drop model" is assumed as a structural model of a lipoprotein particle with reference to the following reference literatures to calculate the concentration of CE or FC or the concentration of lipoprotein particles in a subject sample in the present embodiment.

(1) Yang C Y, Gu Z W, Weng S A, Kim T W, Chen S H, Pownall H J, Sharp P M, Liu S W, Li W H, Gotto A M Jr, et al. Structure of apolipoprotein B-100 of human low density lipoproteins. Arteriosclerosis 1989; 9: 96 to 108.

(2) Schumaker V N, Phillips M L, Chatterton J E. Apolipoprotein B and low-density lipoprotein structure: implications for biosynthesis of triglyceride-rich lipoproteins. Adv Protein Chem 1994; 45: 205 to 248.

(3) Segrest J P, Garber D W, Brouillette C G, Harvey S C, Anantharamaiah G M. The amphipathic alpha helix: a multifunctional structural motif in plasma apolipoproteins. Adv Protein Chem 1994; 45: 205 to 248.

(4) McNamara J R, Small D M, Li Z, Schaefer E J. Differences in LDL subspecies involve alterations in lipid composition and conformational changes in apolipoprotein B. J Lipid Res 1996; 37: 1924 to 1935.

Hereinbelow, the oil drop model will be explained with reference to FIGS. 10A and B. The following assumptions are made in the oil drop model.

Being in the form of spherical particles;

The surface layer (S) is composed of phospholipid (PL), apolipoprotein, and free cholesterol (FC);

The core (C) is composed of triglyceride (TG) and cholesterol ester (CE);

The hydrophobic part of apoB, which accounts for about 15 to 20% of apoB in lipoproteins containing apoB, is present in the core;

About one-sixth of FC present in the surface layer is distributed to the core;

Ratios between the volume of the surface layer (S) and the volume of the core (C) are almost constant in lipoproteins having the same particle size;

Ratios (Vfc:Vce+Vtg), which are ratios between the volume (Vfc) occupied by FC in the surface layer (S) and the volume (Vce+Vtg) of the core (C) composed of the volume (Vce) occupied by CE and the volume (Vtg) occupied by TG, are almost constant in lipoproteins having the same particle size;

ApoB, which is a glycoprotein, contains many O-linked glycans. All of these O-linked glycans stick out of the surface layer of spherical lipoprotein particles, and a hydration layer containing glycans (OS, thickness $t_{os}$) forms around the S layer (thickness $t_s$: see FIG. 10A) of lipoproteins containing apoB;

One apoB-containing lipoprotein particle contains one apoB molecule; and

One apoA-I-containing lipoprotein particle contains an average of one or more (preferably an average of one to four, more preferably an average of two to four) apoA-I molecules.

(Conversion Between Weight Concentration and Volume in the Present Embodiment)

Note that lipid in lipoprotein is measured in the unit of weight concentration mg/dL by the lipoprotein analyzer of FIG. 1, whereas the unit is volume in the oil drop model. In order to unify the units, firstly, weight is converted to mole (mM) (i.e., mg/dL×10/molecular weight of lipid), and then converted to volume using the following molecular volumes obtained from partial specific volumes.

The partial specific volume of each molecule can be appropriately obtained from literature values. Examples of the calculated molecular volume of each molecule are shown below.

TG: partial specific volume 1.093, molecular weight 885.45, molecular volume 1.607 nm$^3$ CE: partial specific volume 1.058, molecular weight 651.1, molecular volume 1.1443 nm$^3$ FC: partial specific volume 0.968, molecular weight 386.7, molecular volume 0.6223 nm$^3$ PL: partial specific volume 0.970, molecular weight 775, molecular volume 1.287 nm$^3$ ApoB-100: partial specific volume 0.740, molecular weight 550000, molecular volume 676.1 nm$^3$ ApoB-48: partial specific volume 0.740, molecular weight 264000, molecular volume 324.5 nm$^3$ ApoA-I: partial specific volume 0.740, molecular weight 28300, molecular volume 34.8 nm$^3$ Note that apoB occurs in the forms of apoB-48 and apoB-100, of which apoB-48 is present in CM, which is mainly separated into G01 and G02. Thus, the value of apoB-100 is used as the aforementioned apoB except when the value of apoB-48 is used to calculate the standard Vc of CM (to be described later).

(Calculation of the Concentration of CE in the Present Embodiment)

Further, based on the explanation given above, the method for calculating the concentration of cholesterol ester (CE) in the present embodiment will be further described with reference to FIG. 7.

(Detection of Cho and TG)

Firstly, the concentrations (mg/dl) of total cholesterol (Cho) and triglyceride (TG) contained in subject samples are detected using the lipoprotein analyzer of FIG. 1. The detection method used here is as described above. Also, detection is carried out for each of the above-described fractions, which are defined based on the lipoprotein particle size.

(Calculation of the Concentration of CE)

Next, the concentration of cholesterol ester (CE) is calculated by the arithmetic unit (calculation unit) 10 using the concentrations of Cho and TG thus detected.

Specifically, the concentration of CE is calculated using a modeled relationship among the concentrations of Cho, TG, and CE. Hereinbelow, more specific examples of calculation will be described with reference to FIG. 7.

(Identification of a Regression Equation)

Firstly, given that Cho is composed of CE, which is bound to fatty acids, and FC, which is not bound to fatty acids, the ratio CE/Cho, which is a ratio of the actual value of CE to the actual value of Cho, is assumed to be y. Meanwhile, the ratio Cho/(Cho+TG), which is a ratio of the actual value of Cho to the sum of the actual values of Cho and TG, which are the main components of lipoprotein, is assumed to be x. A model was examined based on the assumption that, in understanding lipoprotein structure, there was a correlation between x and y. As a result, it was found that the correlation between x and y fit into the following inverse function.

$$y = b_1 \times 1/x + b_0 \quad (0 < x \leq 1.0, y \geq 0) \tag{1}$$

The results of fitting of each of the fractions G06, G09, and G17 are shown with the values of the coefficient $b_1$ and constant $b_0$ in FIG. 7.

The data of actual values used for fitting in FIG. 7 were obtained from 80 healthy individuals. Also, arrows in FIG. 7 indicate the average values of 80 healthy individuals, which were used as the anchor points. In this fitting, the conditions were set as follows: the curve representing the regression equation must pass through the anchor point; the number of Cho molecules is the sum of the numbers of CE molecules and FC molecules; and all of the assumptions made in the oil drop model (particularly, an assumption that ratios between the volume Vfcs, which is the volume of FCs, which is FC present in the lipoprotein surface layer (S), and the volume (Vce+Vtg), which is the volume of CE+TG, are almost constant in lipoproteins having the same particle size) are satisfied.

In more detail, the number of Cho molecules being the sum of the numbers of CE molecules and FC molecules is synonymous with the following: that is, supposing that the fatty acid moiety of CE is oleic acid, when the molecular weight of Cho and FC is 386.7 and the molecular weight of CE is 651.1, the following equations are obtained.

Cho concentration/386.7=FC concentration/386.7+CE concentration/651.1

FC concentration=Cho concentration−CE concentration/1.684

Also, considering that "as a result of conversion to weight concentration, the weight concentration (mg/dl) ratio of FC, CE, and TG per mole is 386.7:651.1:885.45=1:1.684:2.290, and similarly the molecular volume ratio is 0.6223:1.1443:1.607=1:1.8388:2.582", the volume ratio Vfcs:(Vce+Vtg) being constant (Vfcs/(Vce+Vtg)=A (constant number)) is synonymous with the ratio between the concentration of FCs and the concentration of CE×1.09+the concentration of TG×1.127 being constant (i.e., FCs concentration/(CE concentration×1.09+TG concentration×1.127)=A). Further, comparison between the weight concentration ratios (FCs concentration/(CE concentration+TG concentration)=B) based on the actual values of each of the fractions G01 to G20 obtained from a group of 80 healthy individuals and the volume ratios A calculated from the aforementioned actual values is shown in Table 1. Note that in Table 1, G20$^b$ indicates the value of fraction G20 that has been subjected to background correction (to be described later). The values of A and B are almost equal, indicating that weight concentration ratios can approximate volume ratios. Further, there are little variations in weight ratios and in volume ratios in each fraction, indicating that the volume ratios Vfcs: (Vce+Vtg) being constant in lipoproteins having the same particle size can be rephrased as the ratios between the concentration of FCs and the concentration of CE+the concentration of TG being constant.

TABLE 1

| | Group of healthy individuals (n = 80) | | | | |
|---|---|---|---|---|---|
| | Constant A (volume ratio) | | Constant B (weight ratio) | | |
| Fraction | Average value | 95% Confidence interval of the average value | Average value | 95% Confidence interval of the average value | B/A |
| CM (G01 + 02) | 0.013 | 0.010-0.017 | 0.015 | 0.011-0.018 | 1.119 |
| G03 | 0.031 | 0.029-0.033 | 0.034 | 0.032-0.037 | 1.118 |
| G04 | 0.043 | 0.040-0.046 | 0.048 | 0.045-0.051 | 1.119 |
| G05 | 0.063 | 0.060-0.066 | 0.071 | 0.067-0.074 | 1.117 |
| G06 | 0.091 | 0.087-0.095 | 0.101 | 0.097-0.105 | 1.112 |
| G07 | 0.146 | 0.133-0.158 | 0.161 | 0.147-0.174 | 1.104 |
| G08 | 0.169 | 0.160-0.179 | 0.186 | 0.175-0.197 | 1.097 |
| G09 | 0.174 | 0.168-0.179 | 0.190 | 0.184-0.196 | 1.095 |
| G10 | 0.156 | 0.146-0.167 | 0.171 | 0.160-0.183 | 1.095 |
| G11 | 0.148 | 0.132-0.164 | 0.162 | 0.145-0.179 | 1.096 |
| G12 | 0.148 | 0.132-0.164 | 0.162 | 0.145-0.180 | 1.097 |
| G13 | 0.136 | 0.125-0.148 | 0.150 | 0.137-0.163 | 1.097 |
| G14 | 0.107 | 0.100-0.114 | 0.117 | 0.109-0.125 | 1.096 |
| G15 | 0.094 | 0.080-0.108 | 0.103 | 0.087-0.119 | 1.096 |
| G16 | 0.082 | 0.077-0.088 | 0.090 | 0.084-0.096 | 1.095 |
| G17 | 0.096 | 0.092-0.100 | 0.105 | 0.101-0.109 | 1.095 |
| G18 | 0.120 | 0.114-0.126 | 0.132 | 0.125-0.138 | 1.095 |
| G19 | 0.176 | 0.164-0.189 | 0.193 | 0.180-0.207 | 1.097 |
| G20$^b$ | 0.702 | 0.611-0.792 | 0.766 | 0.667-0.865 | 1.092 |

Also, formula (1) can be converted to the following linear equation by replacing 1/x in formula (1) with x'.

$$y = b_1 \times x' + b_0 \quad (x' \geq 1.0, y > 0) \tag{2}$$

That is, formulae (1) and (2) are equivalent. Using formula (2), fitting can be carried out under the same conditions as formula (1) (FIG. 8). Arrows in FIG. 8 indicate the average values of 80 healthy individuals, which are the anchor points.

As to the fitting conditions, various conditions can be used besides those specified above, and the values of $b_1$ and $b_0$ in formula (1) or (2) vary depending on the conditions. Table 2 below shows the ranges of possible values of $b_1$ and $b_0$ in each of the fractions G01 to G20 when the anchor points determined from the average values of the actual values obtained from 80 healthy individuals under the aforementioned conditions are shifted within a 95% confidence interval. The values of the coefficient $b_1$ and constant $b_0$ in the aforementioned formula (1) or (2) in each fraction defined based on the lipoprotein particle size can be set in such a way that these values are contained within the range of Table 2 below. Note that in Table 2, G20$^b$ indicates the value of fraction G20 that has been subjected to background correction (to be described later).

TABLE 2

| Fraction | $b_1$ Range | $b_0$ Range |
|---|---|---|
| CM (G01 + 02) | −0.0302−−0.0187 | 1.6572-1.6694 |
| G03 | −0.0606−−0.0510 | 1.6424-1.6474 |
| G04 | −0.0809−−0.0705 | 1.6253-1.6341 |
| G05 | −0.1106−−0.1015 | 1.6067-1.6129 |
| G06 | −0.2264−−0.1402 | 1.5277-1.5870 |
| G07 | −0.2264−−0.1985 | 1.5277-1.5467 |
| G08 | −0.2484−−0.2278 | 1.5127-1.5267 |
| G09 | −0.2478−−0.2367 | 1.5131-1.5207 |
| G10 | −0.2353−−0.2119 | 1.5217-1.5376 |
| G11 | −0.2317−−0.1958 | 1.5241-1.5486 |
| G12 | −0.2322−−0.1960 | 1.5237-1.5484 |
| G13 | −0.2147−−0.1868 | 1.5357-1.5597 |

TABLE 2-continued

| Fraction | $b_1$ Range | $b_0$ Range |
|---|---|---|
| G14 | −0.1738−−0.1553 | 1.5636-1.5762 |
| G15 | −0.1664−−0.1251 | 1.5687-1.5947 |
| G16 | −0.1389−−0.1238 | 1.5874-1.5977 |
| G17 | −0.1552−−0.1450 | 1.5763-1.5832 |
| G18 | −0.1888−−0.1740 | 1.5534-1.5635 |
| G19 | −0.2583−−0.2312 | 1.5060-1.5299 |
| G20[b] | −0.5927−−0.2488 | 1.2778-1.5157 |

Using formula (1) or (2), the ratio of actual CE/actual Cho in each fraction gives rise to a function of only the actual values of Cho and TG in each fraction. Thus, using this regression equation, the values of CE (calculated values of CE) can be calculated from the actual Cho and TG without directly measuring the actual values of CE.

Note that the values of CE and FC are convertible to each other using the aforementioned conversion formula. Thus, from the viewpoint of calculation processing, both of CE and FC can almost equally be the objects of calculation.

Scatter plots of 80 healthy individuals for the fractions G06, G09, and G17 are shown in FIG. 9, in which the calculated values of CE obtained using formula (1) is defined as y and the actual values of CE is defined as x. A remarkably high correlation was confirmed with a correlation coefficient r>0.987.

Also, with respect to the calculated values of CE obtained from the actual values of Cho of 80 healthy individuals and the actual values of CE, the average values±SD, 95% confidence intervals, and the correlation coefficients of the actual values of CE and the calculated values of CE are shown in Table 3 below. A high correlation was obtained in all fractions with r>0.961 except fraction G20 containing preβ1HDL, in which the application of the oil drop model is difficult. Note that in Table 3, G20[b] indicates the value of fraction G20 that has been subjected to background correction (to be described later).

TABLE 3

| | Actual values of CE in the group of healthy individuals (n = 80) (mg/dL) | | | | Calculated values of CE in the group of healthy individuals (n = 80) (mg/dL) | | | | Correlation coefficient (r) |
|---|---|---|---|---|---|---|---|---|---|
| Fraction | Average value | ± | Standard deviation | 95% Confidence interval of the average value | Average value | ± | Standard deviation | 95% Confidence interval of the average value | |
| CM (G01 + 02) | 0.25 | ± | 0.53 | 0.12-0.39 | 0.25 | ± | 0.54 | 0.11-0.40 | 0.9995 |
| G03 | 0.74 | ± | 1.07 | 0.50-0.99 | 0.74 | ± | 1.11 | 0.49-0.99 | 0.9990 |
| G04 | 2.03 | ± | 2.20 | 1.53-2.54 | 2.03 | ± | 2.31 | 1.51-2.56 | 0.9965 |
| G05 | 4.91 | ± | 3.24 | 4.18-5.65 | 4.90 | ± | 3.25 | 4.16-5.63 | 0.9864 |
| G06 | 9.85 | ± | 5.30 | 8.67-11.03 | 9.84 | ± | 5.24 | 8.67-11.00 | 0.9879 |
| G07 | 17.97 | ± | 8.91 | 15.95-19.99 | 17.79 | ± | 7.95 | 15.99-19.60 | 0.9823 |
| G08 | 37.69 | ± | 12.09 | 34.89-40.49 | 37.18 | ± | 11.15 | 34.60-39.77 | 0.9793 |
| G09 | 42.34 | ± | 10.81 | 39.93-44.74 | 43.55 | ± | 11.00 | 41.10-46.00 | 0.9889 |
| G10 | 28.15 | ± | 8.93 | 26.12-30.18 | 27.90 | ± | 8.49 | 25.97-29.82 | 0.9747 |
| G11 | 10.23 | ± | 3.99 | 9.33-11.14 | 10.12 | ± | 3.53 | 9.31-10.92 | 0.9623 |
| G12 | 2.87 | ± | 1.04 | 2.63-3.10 | 2.83 | ± | 0.87 | 2.64-3.03 | 0.9612 |
| G13 | 0.91 | ± | 0.33 | 0.84-0.98 | 0.91 | ± | 0.29 | 0.84-0.97 | 0.9793 |
| G14 | 1.98 | ± | 0.92 | 1.77-2.19 | 1.96 | ± | 0.86 | 1.76-2.15 | 0.9940 |
| G15 | 6.40 | ± | 6.48 | 4.87-7.92 | 6.39 | ± | 6.42 | 4.89-7.90 | 0.9975 |
| G16 | 26.76 | ± | 13.84 | 23.62-29.90 | 26.71 | ± | 14.20 | 23.48-29.93 | 0.9965 |
| G17 | 32.00 | ± | 6.81 | 30.49-33.52 | 31.99 | ± | 6.91 | 30.45-33.53 | 0.9894 |
| G18 | 19.15 | ± | 4.87 | 18.07-20.23 | 19.15 | ± | 4.39 | 18.17-20.12 | 0.9818 |
| G19 | 4.33 | ± | 2.00 | 3.88-4.78 | 4.32 | ± | 1.64 | 3.95-4.69 | 0.9869 |
| G20[b] | 1.32 | ± | 0.41 | 1.23-1.42 | 1.27 | ± | 0.23 | 1.22-1.32 | 0.5020 |

Further, the measured values of samples of apoE2/2 (type III), which is rare dysbolism, samples of lipoprotein lipase (LPL) deficiency and the like with very high TG (>1200 mg/dL), and samples of CETP deficiency were plotted in FIG. 7. As a result, it is found that these values are scattered within the range of the regression equation of formula (1). Meanwhile, with regard to the samples of lecithin cholesterol acyltransferase (LCAT) deficiency, primary biliary cirrhosis (PBC), and the like, the measured values of Lp(Y) (G09), which is known to be TG-rich spherical LDL particles, are scattered within the range of the regression equation, whereas the measured values of Lp(X) (G06 and G19), which is not in the form of spherical particles but in the form of sac-like or disc-like particles, are drastically fall out of the range of the regression equation because these particles do not conform to the oil drop model. It can be assumed that these results verify the validity of the oil drop model and the model regression equation of the present embodiment.

Thus, according to the method of the present embodiment, the concentration of CE (or concentration of FC) can be calculated with high reliability using the actual concentrations of Cho and TG. Hence, without measuring the concentrations of CE or FC, the values thus obtained can be used beneficially for diagnosis and various types of research.

Moreover, since the measurement of the concentrations of CE or FC can be omitted, the method of the present embodiment has a practical advantage that time and cost needed to obtain these values can be reduced.

Further, according to the present embodiment, the aforementioned concentrations of CE and FC can be calculated for each fraction (for example, for each of the aforementioned 20 fractions or for each major class, which is an integration of some fractions). Furthermore, according to the present embodiment, it is also possible to calculate the concentrations of CE and FC as an integrated value by summing the values of some fractions using the concentrations of CE and FC calculated for each fraction. Thus, the present embodiment enables diagnosis and the like utilizing various values obtained as above. Further, according to the present embodiment, it is also possible to calculate the concentration of lipoprotein particles as shown below by utilizing the knowledge that the lipoprotein particle diameter is specified in each fraction.

(Method for Calculating the Concentration of Lipoprotein Particles)

Next, the method for calculating the concentration of lipoprotein particles (unit: M) will be described.

As understood from the aforementioned Patent Literature 3 of the present inventor, it can be assumed that the particle size of lipoproteins belonging to a certain fraction is almost constant (this point will be described in detail later). In light of this, the concentration of particles belonging to a certain fraction can be calculated by dividing the sum (tVc) of the core volume of all lipoprotein particles in the fraction by the core volume (standard Vc) of one lipoprotein particle.

Note that $$tVc = tVtg + tVce + tFcc;$$

tVc: Sum of the core volume of all lipoproteins in the fraction;

tVtg: Sum of the volume of triglycerides in the cores of all lipoproteins in the fraction;

tVce: Sum of the volume of cholesterol esters in the cores of all lipoproteins in the fraction;

tVfcc: Sum of the volume of free cholesterols in the cores of all lipoproteins in the fraction; and Standard Vc: Volume of the core of one lipoprotein particle in the fraction.

(Calculation of tVc)

The concentration of lipoproteins in an arbitrary fraction measured by the lipoprotein analyzer of FIG. 1 is converted to volume by the aforementioned method. According to the assumptions made in the oil drop model, about one-sixth of FC in the surface layer of lipoprotein particle is distributed to the core, and thus, the actual total volume (tVc) of the cores of lipoproteins in each fraction is the sum of the total volume of TG (tVtg), the total volume of CE (tVce), and the total volume of FC distributed to the core (tVfcc).

More specifically, $$tVtg = TG(\text{mg/dL})/88.545 \times 1.607(\text{nm}^3)$$

$$tVce = CE(\text{mg/dL})/65.11 \times 1.1443(\text{nm}^3)$$

$$tVfcc = [FC(\text{mg/dL})/38.67 \times 0.6223(\text{nm}^3)] \times 1/6$$

According to the above equations, tVc can be calculated as long as the measured or calculated concentrations of TG, CE, and FC in an arbitrary fraction are known.

(Calculation of Standard Vc)

According to the method for analyzing lipoproteins described in the aforementioned Patent Literature 3 of the present inventor, twenty fractions were defined based on the particle size. Fractions separated in accordance with component peaks 1 to 20 in the above literature are provided as G01 to G20. Although the size of the twenty fractions is defined with diameter (nm) in the literature, the radius ($R_{hplc}$, unit nm) will be used in the following description. The assumptions used for calculation are summarized below.

Separation of lipoproteins by gel filtration depends on the differences in the size of the maximum hydration layer of lipoprotein particle (the maximum size including an amorphous hydration layer formed by glycans: see FIGS. 10A and B). Accordingly, the particle size (Rhplc) in G01 to G20 defined by the aforementioned gel filtration is synonymous with the size of the maximum hydration layer of lipoprotein particle.

The volume (standard Vc) occupied by the core in one particle is constant in lipoprotein particles having a constant size, and this volume can be calculated by the following formulae (3) and (4) using the core radius ($R_c$, unit nm) in the fractions G01 to G20 defined by $R_{hplc}$:

$$\text{Standard } Vc(\text{nm}^3) = 4/3\pi R_c^3(\text{nm}^3) - apoB \text{ molecular volume} \times (0.15 \text{ to } 0.20) \quad (3)$$

$$R_c(\text{nm}) = R_{hplc} - t_s - t_{os} \quad (4)$$

Here, based on the literature values, etc., the following values are determined: $t_s = 2.3$ nm, $t_{os} = 1.0$ to $1.4$ nm (apoB-containing lipoprotein) or 0 to 0.6 nm (non-apoB-containing lipoprotein)

Note that apoB-containing lipoproteins are present in G01 to G13, forming the OS layer via glycans contained in apoB (see FIG. 10A). Meanwhile, among non-apoB-containing lipoproteins, spherical particles are HDL particles present in G14 to G20. There particles contain one or more apoA-I in the S layer, and these apoA-I do not contain glycans. Therefore, the apoB molecular volume is 0, and the OS layer may not always be formed because these apoA-I lack glycans. However, HDL fractions may contain apolipoproteins containing glycans other than apoA-I. For example, apolipoprotein E contains O-linked glycans and forms the OS layer, and in view of this, 0.2 to 0.6 nm is deducted for $t_{os}$ (see FIG. 10B) in the relevant fractions.

(Correction of Calculation of Standard Vc in G01-G02)

Note that G01, which is separated as the excluded volume of the column in the method for analyzing lipoproteins described in the aforementioned Patent Literature 3 of the present inventor, is integrated with G02 to be provided as a CM fraction equivalent. The core radius $R_c$ for the CM fraction equivalent can be calculated as follows:

using the diameter in G01 (the original definition of size, $R_{hplc} > 90$ nm and the diameter of 75 nm in G02, and further using a histogram of a detection curve for TG, which is the major lipid component of CM, in G01 and G02 obtained from 80 healthy individuals, obtain a weighted average size. For example, the core radius $R_c$ can be calculated as 41.2 nm ($R_{hplc}$).

That is, for example, when $t_o = 2.3$ nm and $t_{os} = 1.4$ nm, Vc in G01+G02 can be calculated as follows.

$$\text{Standard } V_c(G01+G02) = 4/3 \times \pi \times (41.2 - 2.3 - 1.4)^3 - 324.5 \times 0.2 \text{ nm}^3$$

(Background Correction of G20)

Also, the chromatogram curve detected for fraction G20 contains colored blood components. In view of this, background correction is performed to correct the detected values of TG and Cho in fraction G20, and the thus corrected values are used as the aforementioned $G20^b$. In a chromatogram obtained by passing an eluent instead of an enzyme reagent, a background peak X appears near the range of the normal size of fraction G20. For the detection of TG, 21 peaks including peak X are generated by adding peak X into separated peaks having twenty fractions by Gaussian approximation, using the time and width of peak X, followed by deduction of peak X as a background. As to the background in the detection of Cho, the area of peak X in the detection pattern of TG is deducted when the detection wavelength or color source of enzyme reagent are the same as those in the detection of TG. When the detection wavelength or color source in the detection of Cho is different from those in the detection of TG, adjustment will be necessary. In many cases, the area of peak X corresponds to 80 to 90% of the area of fraction G20 in a chromatogram for the detection of TG. In light of this, 80 to 90% of the detected values of TG in G20 are deducted here based on the assumption that these values reflect the colored blood components. Also, with respect to the detected values of Cho, an area corresponding to 80 to 90% of the detected values of TG is deducted from the chromatogram curve. The background-corrected value is provided as $G20^b$, and the thus corrected concentration of TG (mg/dL) or Cho is used.

Examples of the standard Vc (core standard volume) of G06, G09, and G17 calculated in accordance with the aforementioned calculation method are 13180 $nm^3$, 2980 $nm^3$, and 128 $nm^3$, respectively. However, standard Vc varies depending on the conditions of $R_{hplc}$, $t_s$, $t_{os}$, and the like. Ranges of preferable possible values of standard Vc in each of the fractions G01 to G20 under the aforementioned conditions are shown in Table 4. Namely, standard Vc in each fraction defined based on the particle size of lipoprotein can be set at a value encompassed by the range of Table 4.

TABLE 4

| Fraction | Diameter (nm) Definition | Radius (nm): Rhplc | Range of the core standard volume (Vc) ($nm^3$) |
|---|---|---|---|
| CM (G01 + 02) | 82.4 | 41.2 | 220646-224265 |
| G03 | 64 | 32 | 94756-96850 |
| G04 | 53.6 | 26.8 | 51471-52891 |
| G05 | 44.5 | 22.25 | 26589-27530 |
| G06 | 36.8 | 18.4 | 13164-13782 |
| G07 | 31.3 | 15.65 | 7009-7442 |
| G08 | 28.6 | 14.3 | 4851-5206 |
| G09 | 25.5 | 12.75 | 2968-3246 |
| G10 | 23 | 11.5 | 1852-2076 |
| G11 | 20.7 | 10.35 | 1096-1278 |
| G12 | 18.6 | 9.3 | 715-769 |
| G13 | 16.7 | 8.35 | 438-620 |
| G14 | 15 | 7.5 | 408-539 |
| G15 | 13.5 | 6.75 | 278-369 |
| G16 | 12.1 | 6.05 | 187-221 |
| G17 | 10.9 | 5.45 | 107-131 |
| G18 | 9.8 | 4.9 | 57.9-73.6 |
| G19 | 8.8 | 4.4 | 28.7-38.8 |
| $G20^b$ | 7.6 | 3.8 | 11.5-14.1 |

Note that FIG. 11 comparatively shows the results of calculating the particle concentration by the method of the present embodiment using the actual values obtained using an XL column (TSKgel Lipropak XL column) and a silica column (SkylightPak-LDL column) as the column of the lipoprotein analyzer. Also, FIG. 12 comparatively shows similar results obtained with an XL column and a Sup column (Superose 6HR 10/30 column). As understood from these results, even when different types of columns are used, there is only very little difference in the values of the particle concentration obtained. Accordingly, the method of the present embodiment can be carried out independently of the type of a column. However, G01 obtained with an XL column, G04 obtained with a silica column, and G06 and larger fractions obtained with a Sup column are affected by the excluded volume of the column, and therefore, integration or adjustment will be necessary in these fractions.

Further, FIG. 14 on the left shows the correlation between the actual concentration of apoB molecules and the calculated concentration of apoB-containing lipoprotein particles as obtained in the present embodiment, and FIG. 14 on the right shows the correlation between the actual concentration of apoA-I molecules and the calculated concentration of apoA-I-containing lipoprotein particles as obtained in the present embodiment. The concentration ratio in the former correlation is roughly 1:1, and that in the latter correlation is roughly 2.8:1, and these results are consistent with the oil drop model.

(Identification of a Quadratic Regression Equation Reflecting a Core Composition Ratio)

A ratio of CE to the core composed of TG and CE in the oil drop model is defined as a core composition ratio (core CE %), and is expressed as the actual CE/(the actual TG+the actual CE)×100(%). The core CE % reflects each individual's lipoprotein metabolism, and is assumed to vary among fractions. According to another embodiment of the present disclosure, by defining the actual core CE % as y', the relationship between y' and x in formula (1) involving actual measurement is fitted into the following quadratic regression equation. Assuming that x''=x×100, $$y' = b_2 \times x''^2 + b_1' \times x'' + b_0' \quad (0 < x'' \leq 100, 0 \leq y' \leq 100) \quad (5)$$

By formula (5), the actual core CE % can be expressed as a quadratic equation in which x×100, namely, the combined variable of the actual Cho and the actual TG, Cho/(Cho+TG)×100, is set as the variable. Accordingly, x can be said to be a value reflecting core CE % (a value that changes with changes in core CE %).

FIG. 13 shows the results of fitting in fractions G06, G09, and G17, along with the values of the coefficients $b_2$ and $b_1'$ and constant $b_0'$ used. According to FIG. 13, it is found that the data points obtained from the group of healthy individuals are scattered within the approximated curve of the model of formula (5).

The data of actual values used in FIG. 13 were obtained from 80 healthy individuals. Also, arrows in FIG. 13 indicate the average values of 80 healthy individuals, which were used as the anchor points. The conditions were set as follows: the curve representing the quadratic regression equation must pass through the anchor point; the number of Cho molecules is the sum of the numbers of CE molecules and FC molecules; and all of the assumptions made in the oil drop model (particularly, an assumption that ratios between the volume Vfcs, which is the volume of FCs, which is FC present in the lipoprotein surface layer (S), and the volume (Vce+Vtg), which is the volume of CE+TG, are constant in lipoproteins having the same particle size) are satisfied.

Further, the measured values of samples of apoE2/2 (type III), which is rare metabolic disorder, samples of lipoprotein lipase (LPL) deficiency and the like with very high TG (>1200 mg/dL), and samples of CETP deficiency were plotted in FIG. 13. As a result, it is found that these values are scattered within the range of the regression equation of formula (5). Meanwhile, with regard to the samples of lecithin cholesterol acyltransferase (LCAT) deficiency, primary biliary cirrhosis (PBC), and the like, the measured values of Lp(Y) (G09), which is known to be TG-rich spherical LDL particles, are scattered within the range of the regression equation, but the measured values of Lp(X) (G06 and G19), which is not in the form of spherical particles but in the form of sac-like or disc-like particles, are drastically fall out of the range of the regression equation because these particles do not conform to the oil drop model. It can be assumed that these results verify the validity of the oil drop model and the model regression equation of the present embodiment.

In the following Table 5, the range of possible calculated values of x" based on the assumption of the oil drop model in the model of formula (5) and the range of the values of x" obtained using the actual values obtained from a large-scale study of general health checkup are shown. It is confirmed that x" in the model of formula (5) can fully cover the range of x" obtained from the large-scale group. Also, in 80 healthy individuals, the correlation coefficients (quadratic equations) of the actual values of core CE % (y') and the values reflecting core CE % (x") in each fraction are shown in Table 5. A remarkably high correlation of r>0.93 was demonstrated in all fractions except G20.

As a fundamental rule, one apoB-containing lipoprotein particle contains one apoB molecule (oil drop model). Therefore, the number of apoB molecules in the serum is considered to be nearly equal to the total number of lipoprotein particles in the fractions of apoB-containing lipoproteins (G1 to G13). Firstly, with respect to the group of healthy individuals (control), the relationship (regression equation) between the actual value of the concentration of apoB molecules and the total number of particles in G1 to G13 as calculated according to the present embodiment is obtained, and using the actual value of the concentration of apoB molecules in the CEPT-deficient group and the aforementioned regression equation, an ideal total number of particles (ideal number of particles) in G1 to G13 is calculated. Then, with respect to the CEPT deficient group, the aforementioned ideal number of particles is subtracted from the total number of particles in G1 to G13 as calculated according to the present embodiment to obtain the number of giant HDL particles mixed into the fractions of very small LDL (G11 to G13). Further, the corrected number of very small LDL (corrected G11 to g13) particles can be calculated by subtracting the number of giant HDL particles from the number of very small LDL (G11 to G13) particles before correction as calculated according to the present embodiment. FIG. 15 shows the results of the correction of the correlation between the weight concentration of apoB and

TABLE 5

| | Value reflecting core CE % (oil drop model) | | | Group of healthy individuals (n = 80) | | | | | | | Group of large-scale health checkup subjects (n = 1568) Value reflecting core CE %: TC/(TC + TG) % | | |
|---|---|---|---|---|---|---|---|---|---|---|---|---|---|
| | | | | Core CE %: CE/(CE + TG) % | | | Value reflecting core CE %: TC/(TC + TG) % | | | | | | |
| Fraction | Minimum value | - | Maximum value | Average | Minimum value | - | Maximum value | Average | Minimum value | - | Maximum value | Correlation coefficient r | Average value | Minimum value | - | Maximum value |
| CM (G01 + 02) | 1.42 | - | 100.00 | 17.57 | 2.93 | - | 47.28 | 12.97 | 2.77 | - | 37.16 | 0.9915 | 19.72 | 4.00 | - | 80.00 |
| G03 | 3.63 | - | 100.00 | 23.88 | 1.29 | - | 67.49 | 19.09 | 3.63 | - | 56.47 | 0.9925 | 21.98 | 6.90 | - | 69.57 |
| G04 | 5.00 | - | 100.00 | 20.01 | 7.29 | - | 36.05 | 17.40 | 7.05 | - | 30.49 | 0.9839 | 23.27 | 8.33 | - | 70.18 |
| G05 | 6.43 | - | 100.00 | 24.79 | 10.53 | - | 57.27 | 22.61 | 12.00 | - | 49.30 | 0.9910 | 32.55 | 14.41 | - | 83.05 |
| G06 | 8.86 | - | 100.00 | 38.34 | 18.57 | - | 64.08 | 35.05 | 18.26 | - | 58.85 | 0.9955 | 36.59 | 16.53 | - | 80.53 |
| G07 | 13.06 | - | 100.00 | 63.48 | 35.13 | - | 81.39 | 59.87 | 38.87 | - | 78.23 | 0.9482 | 58.05 | 19.70 | - | 88.73 |
| G08 | 15.77 | - | 100.00 | 80.72 | 68.74 | - | 88.50 | 77.61 | 63.08 | - | 86.07 | 0.9680 | 72.71 | 21.05 | - | 91.89 |
| G09 | 15.93 | - | 100.00 | 85.08 | 73.77 | - | 92.41 | 82.34 | 70.58 | - | 90.85 | 0.9915 | 80.71 | 26.45 | - | 92.44 |
| G10 | 14.63 | - | 100.00 | 85.91 | 74.93 | - | 92.62 | 82.91 | 71.49 | - | 90.15 | 0.9633 | 81.07 | 32.35 | - | 93.00 |
| G11 | 13.42 | - | 100.00 | 84.41 | 68.26 | - | 91.07 | 81.10 | 65.67 | - | 87.77 | 0.9365 | 79.04 | 36.27 | - | 96.07 |
| G12 | 13.37 | - | 100.00 | 82.79 | 59.58 | - | 90.86 | 79.41 | 55.41 | - | 87.63 | 0.9633 | 78.19 | 30.61 | - | 96.91 |
| G13 | 12.31 | - | 100.00 | 82.86 | 46.63 | - | 100.00 | 79.42 | 41.89 | - | 100.00 | 0.9915 | 75.43 | 30.10 | - | 94.80 |
| G14 | 10.37 | - | 100.00 | 84.08 | 55.07 | - | 94.59 | 79.79 | 47.73 | - | 93.20 | 0.9955 | 74.26 | 22.95 | - | 95.15 |
| G15 | 7.92 | - | 100.00 | 85.80 | 61.27 | - | 96.61 | 81.47 | 52.58 | - | 95.24 | 0.9803 | 71.03 | 19.76 | - | 91.30 |
| G16 | 8.60 | - | 100.00 | 85.18 | 68.72 | - | 93.80 | 80.25 | 59.63 | - | 91.61 | 0.9940 | 72.95 | 21.60 | - | 92.46 |
| G17 | 9.48 | - | 100.00 | 85.41 | 68.97 | - | 93.91 | 80.86 | 61.57 | - | 92.01 | 0.9975 | 76.33 | 26.15 | - | 92.96 |
| G18 | 11.34 | - | 100.00 | 86.05 | 67.43 | - | 93.96 | 82.32 | 63.27 | - | 92.28 | 0.9930 | 78.56 | 32.12 | - | 92.93 |
| G19 | 15.05 | - | 100.00 | 82.50 | 59.01 | - | 91.56 | 79.87 | 59.69 | - | 89.13 | 0.9767 | 79.52 | 36.61 | - | 96.59 |
| G20[b] | 16.32 | - | 100.00 | 94.55 | 87.84 | - | 97.48 | 96.05 | 86.42 | - | 98.10 | 0.7563 | 93.40 | 47.42 | - | 97.59 |

(Correction in CETP Deficiency)

Cholesterol ester transfer protein (CETP) adjusts the amount and quality of HDL and LDL by transferring cholesterol from HDL to VLDL and LDL. In human patients with CETP deficiency and rats or mice naturally lacking CETP, due to lack of CETP, HDL (normally present in fractions G14 to G20) becomes large in size and mix into the fractions of very small LDL (G11 to G13) as giant HDL. Therefore, the concentrations of very small LDL and giant HDL particles cannot be properly calculated. In order to solve this problem, a correction is made as follows.

the concentration of apoB-containing lipoprotein particles in samples obtained from healthy individuals (control) and patients with CETP deficiency by the aforementioned method. Comparing before and after the correction, it is found that the correlation in samples obtained from the patients with CETP deficiency has been optimized.

Further, for example, it is also possible to obtain the TG+CE volume in giant HDL by multiplying the number of giant HDL particles by the standard Vc in G12, and then obtain the concentrations of TG and CE in giant HDL based on the assumption that the core composition ratio is the same as HDL (for example, G14). Furthermore, the concentrations of TG and CE in corrected G11 to G13 can be obtained by subtracting the concentrations of TG and CE in giant HDL from the concentrations of TG and CE in G11 to G13 before correction as calculated according to the present embodiment.

The aforementioned method of correction can also be applied to calculate, for example, the number of giant Lp(a) particles. Lp(a) particles result from apo(a) binding to apoB by an S—S linkage, and have a similar core composition to LDL. The aforementioned method of correction can also be applied to calculate, for example, the number of giant, aggregated LDL particles resulting from aggregation of LDL due to repeated freezing and thawing.

Further, there is another method of correction as will be described below. The average value of the ratio of the concentration of lipid at peaks (fractions contaminated with giant HDL in CETP deficiency, such as G12 and G13) adjacent to the peak of the lowest valley in the group of healthy individuals (control) (a fraction not contaminated with giant HDL in CETP deficiency, such as G11) are obtained in advance. Then, by multiplying G11 in CETP deficient samples by the ratio thus obtained, the true concentrations of lipid in G12 and G13, which exclude giant HDL mixed in G12 and G13, can be calculated. The concentration of lipid in contaminating giant HDL can be calculated by subtracting the true concentrations of lipid from the actual concentrations of lipid in G12 and G13, and further, from the concentrations of Cho and TG and the regression model and the oil drop model of the present embodiment, the number of particles of respective substances can be calculated. FIG. 16 shows the result of correction of the correlation between the weight concentration of apoB and the concentration of apoB-containing lipoprotein particles in samples obtained from healthy individuals (control) and patients with CETP deficiency by the aforementioned another method of correction. Comparing before and after the correction, it is found that the correlation in samples obtained from the patients with CETP deficiency has been optimized.

(Summary)

Lipoprotein metabolism can be analyzed by each of the aforementioned embodiments. For example, it is revealed that, in fraction G06, the values corresponding to Cho/(Cho+TG) (corresponding to the aforementioned x, x', and x") are scattered in a wide range even in a group of healthy individuals. This is presumed to be due to a large variation in CE % composition ratio in the core, despite the same particle size. Further, the value of CE can be accurately estimated in Lipid Metabolism Disorder, including those conditions that involve CE-rich VLDL (such as type III hyperlipidemia and remnant hyperlipoproteinemia). That is, without actually measuring FC, the value of CE can be accurately estimated using the actual data of Cho and TG obtained by the Cho/TG detection system. Further, as stated earlier, using the value of CE thus obtained, the accurate particle concentration can also be calculated. Further, also with respect to samples containing giant HDL due to CETP deficiency as well as giant aggregated LDL resulting from the aggregation of particles and giant Lp(a) due to the binding of apo(a), the particle concentration, the concentrations of TG and CE, etc. can also be calculated by performing the aforementioned correction.

It is to be noted that the content of the present disclosure is not limited to each of the aforementioned embodiments. Various modifications may be made to the specific configurations of the present disclosure within the description of the scope of the Claims.

REFERENCE NUMERALS LIST

1 Column
2 Splitter
3 First channel
4 Second channel
5 Cho reaction unit
6 TG reaction unit
7 Cho detection unit
8 TG detection unit
9 System controller
10 Arithmetic unit (calculation unit)
11 Sampler
12 First pump
13 Degasser
14 Cho reagent reservoir
15 Second pump
16 TG reagent reservoir The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for analyzing lipoproteins contained in a subject sample, comprising the steps of:
   detecting concentrations of total cholesterol (Cho) and triglyceride (TG) in the lipoproteins for each fraction generated depending on particle size of the lipoproteins, and
   calculating a concentration of cholesterol ester (CE) or free cholesterol (FC) using the concentrations of total cholesterol and triglyceride for each fraction,
   wherein said calculating the concentration of cholesterol ester or free cholesterol is performed using a modeled relationship among the concentrations of total cholesterol, triglyceride, and cholesterol ester or free cholesterol, and
   wherein the modeled relationship is expressed by at least one of the following formulae:

$y = b_1/x + b_0,$ $y = b_1 x' + b_0,$ and $y' = b_2 \times x'^2 + b_1' \times x'' + b_0'$ wherein:
   x is Cho/(Cho+TG),
   y is CE/Cho, $b_1$ is a coefficient obtained by statistical fitting based on actual values from individuals, $b_0$ is a constant obtained by statistical fitting based on actual values from individuals, Cho is the concentration of total cholesterol, TG is the concentration of triglyceride, CE is the concentration of cholesterol ester or free cholesterol, x' is (Cho+TG)/Cho, x" is Cho/(TG+Cho)×100, y' is CE/(TG+CE)×100, $b_2$ is a coefficient obtained by statistical fitting based on actual values from individuals, $b_1'$ is a constant obtained by statistical fitting based on actual values from individuals, and $b_0'$ is a constant obtained by statistical fitting based on actual values from individuals.

2. The method for analyzing lipoproteins according to claim 1, further comprising the step of calculating a concentration of lipoprotein particles that contain the cholesterol ester (CE) therein, wherein the calculation of the particle concentration is performed by tVc/standard Vc, wherein $$tVc=tVtg+tVce+tVfcc;$$

in which:

tVc is the sum of a core volume of all lipoproteins in a fraction of the subject sample;

tVtg is the sum of a volume of triglycerides in cores of all lipoproteins in the fraction of the subject sample;

tVce is the sum of a volume of cholesterol esters in cores of all lipoproteins in the fraction of the subject sample;

tVfcc is the sum of a volume of free cholesterols in cores of all lipoproteins in the fraction of the subject sample; and Standard Vc is the volume of a core of one lipoprotein particle in the fraction of the subject sample.

3. The method for analyzing lipoproteins according to claim 2, wherein the calculation of the particle concentration is carried out for each fraction defined based on the lipoprotein particle size.

4. A lipoprotein analyzer for analyzing lipoproteins contained in the subject sample, comprising:

a detection unit for detecting concentrations of total cholesterol and triglyceride in the lipoproteins for each fraction generated depending on particle size of the lipoproteins, and a calculation unit for calculating a concentration of cholesterol ester or free cholesterol using the concentrations of total cholesterol and triglyceride for each fraction, wherein the calculation of the concentration of cholesterol ester or free cholesterol is performed using a modeled relationship among the concentrations of total cholesterol, triglyceride, and cholesterol ester or free cholesterol, and wherein the modeled relationship is expressed by at least one of the following formulae:

$$y=b_1/x+b_0,$$

$$y=b_1x'+b_0, \text{ and}$$

$$y'=b_2 \times x''^2+b_1' \times x''+b_0'$$

wherein:

x is Cho/(Cho+TG), y is CE/Cho, $b_1$ is a coefficient obtained by statistical fitting based on actual values from individuals, $b_0$ is a constant obtained by statistical fitting based on actual values from individuals, Cho is the concentration of total cholesterol, TG is the concentration of triglyceride, CE is the concentration of cholesterol ester or free cholesterol, x' is (Cho+TG)/Cho, x" is Cho/(TG+Cho)×100, y' is CE/(TG+CE)×100, $b_2$ is a coefficient obtained by statistical fitting based on actual values from individuals, $b_1'$ is a coefficient obtained by statistical fitting based on actual values from individuals, and $b_0'$ is a constant obtained by statistical fitting based on actual values from individuals.

5. A non-transitory computer-readable medium containing an executable computer program for analyzing lipoproteins contained in a subject sample, wherein in response to execution, the executable computer program causes a computer to:

detect concentrations of total cholesterol (Cho) and triglyceride (TG) in the lipoproteins for each fraction generated depending on particle size of the lipoproteins, and calculate a concentration of cholesterol ester (CE) or free cholesterol (FC) using the concentrations of total cholesterol and triglyceride for each fraction, wherein the calculation of the concentration of cholesterol ester or free cholesterol is performed using a modeled relationship among the concentrations of total cholesterol, triglyceride, and cholesterol ester or free cholesterol, and wherein the modeled relationship is expressed by at least one of the following formulae:

$$y=b_1/x+b_0,$$

$$y=b_1x'+b_0, \text{ and}$$

$$y'=b_2 \times x''^2+b_1' \times x''+b_0'$$

wherein:

x is Cho/(Cho+TG), y is CE/Cho, $b_1$ is a coefficient obtained by statistical fitting based on actual values from individuals, $b_0$ is a constant obtained by statistical fitting based on actual values from individuals, Cho is the concentration of total cholesterol, TG is the concentration of triglyceride, CE is the concentration of cholesterol ester or free cholesterol, x' is (Cho+TG)/Cho, x" is Cho/(TG+Cho)×100, y' is CE/(TG+CE)×100, $b_2$ is a coefficient obtained by statistical fitting based on actual values from individuals, $b_1'$ is a coefficient obtained by statistical fitting based on actual values from individuals, and $b_0'$ is a constant obtained by statistical fitting based on actual values from individuals.

* * * * *

UNITED STATES PATENT AND TRADEMARK OFFICE
CERTIFICATE OF CORRECTION

PATENT NO. : 10,048,283 B2
APPLICATION NO. : 15/301916
DATED : August 14, 2018
INVENTOR(S) : Mitsuyo Okazaki It is certified that error appears in the above-identified patent and that said Letters Patent is hereby corrected as shown below:

In the Claims

Column 27, Line 15:
"$b_1'$ is a constant obtained" should read, --$b_1'$ is a coefficient obtained--.

Signed and Sealed this
Thirty-first Day of December, 2019

Andrei Iancu
*Director of the United States Patent and Trademark Office*